United States Patent
Nielsen et al.

(10) Patent No.: US 6,225,310 B1
(45) Date of Patent: *May 1, 2001

(54) FUSED 1,2,4-THIADIAZINE DERIVATIVES, THEIR PREPARATION AND USE

(75) Inventors: Flemming Elmelund Nielsen, Virum; John Bondo Hansen, Jyderup; Holger Claus Hansen, Vaerlose; Tina Møller Tagmose, Ballerup; John Patrick Mogensen, Vanlose, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/539,242

(22) Filed: Mar. 30, 2000

Related U.S. Application Data

(63) Continuation of application No. 09/107,693, filed on Jun. 30, 1998, now abandoned, which is a continuation-in-part of application No. 08/785,438, filed on Jan. 17, 1997, now Pat. No. 5,889,002.

(30) Foreign Application Priority Data

| Jan. 17, 1996 | (DK) | 0041/96 |
|---|---|---|
| Mar. 5, 1996 | (DK) | 0250/96 |
| Mar. 5, 1996 | (DK) | 0251/96 |
| Mar. 5, 1996 | (DK) | 0252/96 |
| Mar. 5, 1996 | (DK) | 0253/96 |
| Mar. 5, 1996 | (DK) | 0256/96 |
| Mar. 5, 1996 | (DK) | 0259/96 |
| Aug. 27, 1996 | (DK) | 0903/96 |
| Jul. 16, 1997 | (DK) | 0872/97 |
| Mar. 17, 1998 | (DK) | 0368/98 |

(51) Int. Cl.$^7$ .................. C07D 498/04; A61K 31/535; A61P 3/10
(52) U.S. Cl. .................................. 514/222.8; 544/10
(58) Field of Search .................... 544/10; 514/222.8

(56) References Cited

U.S. PATENT DOCUMENTS 5,889,002 * 3/1999 Nielsen et al. ............ 514/222.8

FOREIGN PATENT DOCUMENTS

| 0 618 209 A1 | 10/1994 | (EP) . |
| 1 368 948 | 10/1974 | (GB) . |
| WO 97/26265 | 7/1997 | (WO) . |

OTHER PUBLICATIONS

CAS printout for US 5,889,002, Jan. 1997.*
Raffa et al., Farmaco, vol. 29, pp. 411–423 (1974).
Alemzadeh et al., Endocrinology, vol. 133, No. 2, pp. 705–712 (1993).
Hattori et al., The Chemical Society of Japan, vol. 46, No. 6, pp. 1890–1891 (1973).
Stapp, The Journal of Organic Chemistry, vol. 34, No. 4, pp. 1143–1145 (1969).
Williams et al., J. Org. Chem., vol. 38, No. 1, pp. 20–26 (1973).
Press et al., Journal of Medicinal Chem., vol. 22, No. 6, pp. 725–731 (1979).
Roma et al., Eur. J. Med. Chem., vol. 26, pp. 489–496 (1991).
Barnes et al., J.C.S. Chem. Comm., pp. 776–777 (1973).
Topliss et al., J Org Chem, vol. 28, pp. 2313–2319 (1963).
Cronin et al., J Med Chem, vol, 11, pp. 136–139 (1968).
Dillard et al., American Chemical Society, vol. 23, pp. 717–722 (1980).
Meyer, Journal of Heterocyclic Chemistry, vol. 6, pp. 407–408 (1969).
Cheng et al., J. Heterocyclic Chem., vol. 27, pp. 1909–1915 (1990).
Stoss et al., Chem. Ber., vol. 109, pp. 2097–2106 (1976).
Taylor et al., Br. J. Pharmacol., vol. 111, pp. 42–48 (1994).
Arkhammar et al., The Journal of Biological Chemistry, vol. 262, pp. 5448–5454 (1987).
Bellemin et al., J. Heterocyclic Chem., vol. 21, pp. 1017–1021 (1984).
Tamura et al., Chem. Pharm. Bull., vol. 19, pp. 119–123 (1971).
Andersen et al., Chemica Scripta, vol. 29, pp. 45–49 (1989).
Jensen et al., Chemica Scripta, vol. 20, pp. 248–250 (1982).
Kresze et al., Phosphorus and Sulfur, vol. 29, pp. 41–47 (1986).
Ofitserov et al., Khimiia Geterotsiklicheskikh soedinenii, vol. 8, pp. 1119–1122 (1976).
Hamill et al., Pflugers Archiv, vol. 391, pp. 85–100 (1981).
Kotovskaya et al., Plenum Publishing Corporation, vol. 13, pp. 54–57 (1979).
Berge et al., Journal of Pharmaceutical Sciences, vol. 66, pp. 1–19(1977).
Vlahos et al., Metabolism, vol. 40, pp. 825–829 (1991).
Huang et al., J. Med. Chem., vol. 23, pp. 575–577 (1980).
Pirotte et al., J. Med. Chem., Vo.. 36, pp. 3211–3213 (1993).
Pirotte et al., Biochemical Pharmacology, vol. 47, pp. 1381–1386 (1994).

* cited by examiner

*Primary Examiner*—Mukund J. Shah
*Assistant Examiner*—Hong Liu
(74) *Attorney, Agent, or Firm*—Steve T. Zelson, Esq.; Carol E. Rozek, Esq.

(57) ABSTRACT

1,2,4-Thiadiazine and 1,4-thiazine derivates represented by formula (I):

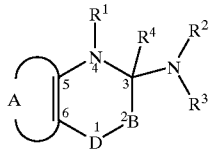

wherein A, B, D, $R^1$, $R^2$, $R^3$ and $R^4$ are defined in the description, compositions thereof and methods for preparing the compounds are described.

The compounds are useful in the treatment of diseases of the central nervous system, the cardiovascular system, the pulmonary system, the gastrointestinal system and the endocrinological system.

3 Claims, No Drawings

FUSED 1,2,4-THIADIAZINE DERIVATIVES, THEIR PREPARATION AND USE

CROSS-REFERENCE TO RELATED APPLICATIONS

This application is a continuation of application Ser. No. 09/107,693 filed on Jun. 30, 1998, now abandoned which is a continuation-in-part of application Ser. No. 08/785,438 filed on Jan. 17, 1997, now U.S. Pat No. 5,889,002 and claims priority under 35 U.S.C. 119 of Danish application nos. 0041/96 filed on Jan. 17, 1996, 0250/96 filed on Mar. 5, 1996, 0251/96 filed on Mar. 5, 1996, 0252/96 filed on Mar. 5, 1996, 0253/96 filed on Mar. 5, 1996, 0256/96 filed on Mar. 5, 1996, 0259/96 filed on Mar. 5, 1996, 0903/96 filed on Aug. 27, 1996, 0872/97 filed on Jul. 16, 1997, and 0368/98 filed on Mar. 17, 1998, the contents of which are fully incorporated herein by reference.

FIELD OF THE INVENTION

The present invention relates to fused 1,2,4-thiadiazine derivatives, to methods for their preparation, to compositions comprising the compounds, to the use of these compounds as medicaments and their use in therapy e.g. in the treatment of diseases of the central nervous system, the cardiovascular system, the pulmonary system, the gastrointestinal system and the endocrinological system.

BACKGROUND OF THE INVENTION

Potassium channels play an important role in the physiological and pharmacological control of cellular membrane potential. Amongst the different types of potassium channels are the ATP-sensitive ($K_{ATP}$-) channels which are regulated by changes in the intracellular concentration of adenosine triphosphate. The $K_{ATP}$-channels have been found in cells from various tissues such as cardiac cells, pancreatic cells, skeletal muscles, smooth muscles, central neurons and adenohypophysis cells. The channels have been associated with diverse cellular functions for example hormone secretion (insulin from pancreatic beta-cells, growth hormone and prolactin from adenohypophysis cells), vasodilation (in smooth muscle cells), cardiac action potential duration, neurotransmitter release in the central nervous system.

Modulators of the $K_{ATP}$-channels have been found to be of importance for the treatment of various diseases. Certain sulphonylureas which have been used for the treatment of non-insulin-dependent diabetes mellitus act by stimulating insulin release through an inhibition of the $K_{ATP}$-channels on pancreatic beta-cells.

The potassium channel openers, which comprise a heterogeneous group of compounds, have been found to be able to relax vascular smooth muscles and have therefore been used for the treatment of hypertension. In addition, potassium channel openers can be used as bronchodilators in the treatment of asthma and various other diseases.

Furthermore, potassium channel openers have been shown to promote hairgrowth, and have been used for the treatment of baldness.

Potassium channel openers are also able to relax urinary bladder smooth muscle and therefore, can be used for the treatment of urinary incontinence. Potassium channel openers which relax smooth muscle of the uterus can be used for treatment of premature labor. By acting on potassium channels of the central nervous system these compounds can be used for treatment of various neurological and psychiatric diseases such as Alzheimer, epilepsy and cerebral ischemia.

Further, the compounds are found to be useful in the treatment of benign prostatic hyperplasia, erectile dysfunction and in contraception.

Compounds of the present invention, which inhibit insulin secretion by activating potassium channels of the beta-cell can be used in combination with other compounds which may be used to treat non-insulin dependent diabetes mellitus and insulin dependent diabetes mellitus. Examples of such compounds are insulin, insulin sensitizers, such as thiazolidinediones, insulin secretagogues, such as repaglinide, tolbutamide, glibenclamide and glucagon like peptide ( GLP1), inhibitors of α-glucosidases and hepatic enzymes responsible for the biosynthesis of glucose.

Recently, it has been shown that Diazoxide (7-chloro-3-methyl-2H-1,2,4-benzothiadiazine 1,1-dioxide) and certain 3-(alkylamino)-4H-pyrido[4,3-e]-1,2,4-thiadiazine 1,1-dioxide derivatives inhibit insulin release by an activation of $K_{ATP}$-channels on pancreatic beta-cells (Pirotte B. et al. *Biochem. Pharmacol*, 47, 1381–1386 (1994); Pirotte B. et al., *J. Med. Chem.*, 36, 3211–3213 (1993). Diazoxide has furthermore been shown to delay the onset of diabetes in BB-rats (Vlahos W D et al. *Metabolism* 40, 39–46 (1991)). In obese zucker rats diazoxide has been shown to decrease insulin secretion and increase insulin receptor binding and consequently improve glucose tolerance and decrease weight gain (Alemzadeh R. et al. Endocrinol. 133, 705–712, 1993). It is expected that compounds which activate $K_{ATP}$-channels can be used for treatment of diseases characterised by an overproduction of insulin and for the treatment and prevention of diabetes.

EP 618 209 discloses a class of pyridothiadiazine derivatives having an alkyl or an alkylamino group in position 3 of the thiadiazine ring. These compounds are claimed to be agonists at the AMPA-glutamate receptor.

In J. Med. Chem. 1980, 23, 575–577 the synthesis of 4(5)-amino-and formylaminoimidazo-5(4) carboxamide and their properties as agents of chemotherapeutic value are described. Especially, the compounds 3-aminoimidazo[4,5-e]-1,2,4-thiadiazine 1,1-dioxide and N-benzoyl-aminoimidazo[4,5-e]-1,2,4-thiadiazine 1,1-dioxide are shown.

DESCRIPTION OF THE INVENTION

The present invention relates to fused 1,2,4-thiadiazine and fused 1,4-thiazine derivatives of the general formula I:

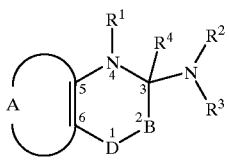

(I)

wherein
B represents >$NR^5$ or >$CR^5R^6$, wherein $R^5$ and $R^6$ independently are hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen; or $R^5$ and $R^4$ together represent one of the bonds in a double bond between the atoms 2 and 3 of formula I;
D represents —$S(=O)_2$— or —$S(=O)$—; or
D—B represents —$S(=O)(R^7)=N$—
wherein $R^7$ is $C_{1-6}$-alkyl; or aryl or heteroaryl optionally mono- or polysubstituted with halogen, hydroxy, $C_{1-6}$- alkoxy, aryloxy, arylalkoxy, nitro, amino, $C_{1-6}$-monoalkyl- or dialkylamino, cyano, acyl, or $C_{1-6}$-alkoxycarbonyl;

$R^1$ is hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen and $R^4$ is hydrogen; or $R^4$ together with $R^5$ represent one of the bonds in a double bond between the atoms 2 and 3 of formula I; or $R^1$ together with $R^4$ represent one of the bonds in a double bond between the atoms 3 and 4 of formula I;

$R^2$ is hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen;

$R^3$ is $R^8$; —$OR^8$; —$C(=X)R^8$; —$NR^8R^9$; bicycloalkyl, aryl, heteroaryl, arylalkyl or heteroarylalkyl optionally mono- or polysubstituted with halogen, hydroxy, $C_{1-6}$-alkoxy, aryloxy, arylalkoxy, nitro, amino, $C_{1-6}$-monoalkyl- or dialkylamino, cyano, oxo, acyl or $C_{1-6}$-alkoxycarbonyl; or aryl substituted with $C_{1-6}$-alkyl;

wherein $R^8$ is hydrogen; $C_{3-6}$-cycloalkyl or ($C_{3-6}$-cycloalkyl)$C_{1-6}$-alkyl, the $C_{3-6}$-cycloalkyl group optionally being mono- or polysubstituted with $C_{1-6}$-alkyl, halogen, hydroxy or $C_{1-6}$-alkoxy; a 3–6 membered saturated ring system comprising one or more nitrogen-, oxygen- or sulfur atoms; or straight or branched $C_{1-18}$-alkyl optionally mono- or polysubstituted with halogen, hydroxy, $C_{1-6}$-alkoxy, $C_{1-6}$-alkylthio, $C_{3-6}$-cycloalkyl, aryl, aryloxy, arylalkoxy, nitro, amino, $C_{1-6}$-monoalkyl- or dialkylamino, cyano, oxo, formyl, acyl, carboxy, $C_{1-6}$-alkoxy-carbonyl, or carbamoyl;

X is O or S;

$R^9$ is hydrogen; $C_{1-6}$-alkyl; $C_{2-6}$-alkenyl; $C_{3-6}$-cycloalkyl optionally mono- or polysubstituted with $C_{1-6}$-alkyl, halogen, hydroxy or $C_{1-6}$-alkoxy; or $R^8$ and $R^9$ together with the nitrogen atom form a 3–12 membered mono- or bicyclic system, in which one or more of the carbon atoms may be exchanged with nitrogen, oxygen or sulfur, each of these ring systems optionally being mono- or polysubstituted with halogen, $C_{1-6}$-alkyl, hydroxy, $C_{1-6}$-alkoxy, $C_{1-6}$-alkoxy-$C_{1-6}$-alkyl, nitro, amino, cyano, trifluoromethyl, $C_{1-6}$-monoalkyl- or dialkylamino, oxo; or $R^3$ is

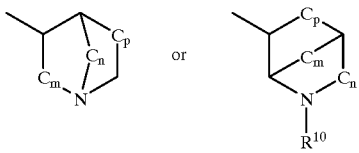

wherein n,m,p independently are 0,1,2,3 and $R^{10}$ is hydrogen; hydroxy; $C_{1-6}$-alkoxy; $C_{3-6}$-cycloalkyl optionally mono- or polysubstituted with $C_{1-6}$-alkyl, halogen, hydroxy or $C_{1-6}$-alkoxy; $C_{1-6}$-alkyl, $C_{2-6}$-alkenyl or $C_{2-6}$-alkynyl optionally mono- or polysubstituted with halogen; or $R^2$ and $R^3$ together with the nitrogen atom forms a 3–12 membered mono- or bicyclic system, in which one or more of the carbon atoms may be exchanged with nitrogen, oxygen or sulfur, each of these ring systems optionally being mono- or polysubstituted with halogen, $C_{1-6}$-alkyl, hydroxy, $C_{1-6}$-alkoxy, $C_{1-6}$-alkoxy-$C_{1-6}$-alkyl nitro, amino, cyano, trifluoromethyl, $C_{1-6}$-monoalkyl- or dialkylamino or oxo;

A together with carbon atoms 5 and 6 of formula I represents a 5 or 6 membered heterocyclic system comprising one or more nitrogen-, oxygen- or sulfur atoms, the heterocyclic systems optionally being mono- or polysubstituted with halogen; $C_{1-12}$-alkyl; $C_{3-6}$-cycloalkyl; hydroxy; $C_{1-6}$-alkoxy; $C_{1-6}$-alkoxy-$C_{1-6}$-alkyl; nitro; amino; cyano; cyanomethyl; perhalomethyl; $C_{1-6}$-monoalkyl- or dialkylamino; sulfamoyl; $C_{1-6}$-alkylthio; $C_{1-6}$-alkylsulfonyl; $C_{1-6}$-alkylsulfinyl; $C_{1-6}$-alkylcarbonylamino; arylthio, arylsulfinyl, arylsulfonyl, the aryl group optionally being mono- or polysubstituted with $C_{1-6}$-alkyl, halogen, hydroxy or $C_{1-6}$-alkoxy; $C_{1-6}$-alkoxycarbonyl; $C_{1-6}$-alkoxycarbonyl-$C_{1-6}$-alkyl; carbamyl; carbamylmethyl; $C_{1-6}$-monoalkyl- or dialkylaminocarbonyl; $C_{1-6}$-monoalkyl- or dialkylaminothiocarbonyl; ureido; $C_{1-6}$-monoalkyl- or dialkylaminocarbonylamino, thioureido; $C_{1-6}$-monoalkyl- or dialkylaminothiocarbonylamino; $C_{1-6}$-monoalkyl- or dialkylaminosulfonyl; carboxy; carboxy-$C_{1-6}$-alkyl; acyl; aryl, arylalkyl, aryloxy, the aryl group optionally being mono- or polysubstituted with $C_{1-6}$-alkyl, halogen, hydroxy or $C_{1-6}$-alkoxy; (1,2,4-oxadiazol-5-yl)- or (1,2,4-oxadiazol-3-yl)-$C_{1-6}$-alkyl the oxadiazolyl group optionally being substituted with $C_{1-6}$-alkyl or $C_{3-6}$-cycloalkyl; or a 5–6 membered nitrogen containing ring, optionally substituted with phenyl or $C_{1-6}$-alkyl;

provided that A together with carbon atoms 5 and 6 of formula I do not form a pyridine ring and that the following compounds 3-aminoimidazo[4,5-e]-1,2,4-thiadiazine 1,1-dioxide and 3-(benzoylamino)imidazo[4,5-e]-1,2,4-thiadiazine 1,1-dioxide are not included;

or a salt thereof with a pharmaceutically acceptable acid or base.

Within its scope the invention includes all optical isomers of compounds of formula I, some of which are optically active, and also their mixtures including racemic mixture thereof.

The scope of the invention also includes all tautomeric forms of the compounds of formula I.

The salts include pharmaceutically acceptable acid addition salts, pharmaceutically acceptable metal salts or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, tartaric, fumaric, mandelic, benzoic, cinnamic, methane-sulfonic, ethane sulfonic, picric and the like, and include acids related to the pharmaceutically acceptable salts listed in Journal of Pharmaceutical Science, 66, 2 (1977) and incorporated herein by reference, or lithium, sodium, potassium, magnesium and the like.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "$C_{1-6}$-alkylthio" as used herein, alone or in combination, refers to a straight or branched monovalent substituent comprising a lower alkyl group linked through a divalent sulfur atom having its free valence bond from the sulfur atom and having 1 to 6 carbon atoms e.g. methylthio, ethylthio, propylthio, butylthio, pentylthio.

The term "$C_{2-6}$-alkenyl" as used herein refers to an unsaturated hydrocarbon chain having 2–6 carbon atoms and one double bond such as e.g. vinyl, 1-propenyl, allyl, isopropenyl, n-butenyl, n-pentenyl and n-hexenyl.

The term "C$_{3-6}$-cycloalkyl" as used herein refers to a radical of a saturated cyclic hydrocarbon with the indicated number of carbons such as cyclopropyl, cyclobutyl, cyclopentyl, or cyclohexyl.

The term "C$_{2-6}$-alkynyl" as used herein refers to unsaturated hydrocarbons which contain triple bonds, such as e.g. —C≡CH, —C≡CCH$_3$, —CH$_2$C≡CH, —CH$_2$CH$_2$C≡CH, —CH(CH$_3$)C≡CH, and the like.

The term "C$_{1-6}$-alkoxy-C$_{1-6}$-alkyl" as used herein refers to a group of 2–12 carbon atoms interrupted by an O such as e.g. CH$_2$—O—CH$_3$, CH$_2$—O—CH$_2$—CH$_3$, CH$_2$—O—CH(CH$_3$)$_2$ and the like.

The term "halogen" means fluorine, chlorine, bromine or iodine.

The term "perhalomethyl" means trifluoromethyl, trichloromethyl, tribromomethyl or triiodomethyl.

The terms "C$_{1-6}$-alkyl", "C$_{1-12}$-alkyl" and "C$_{1-18}$-alkyl" as used herein, alone or in combination, refers to a straight or branched, saturated hydrocarbon chain having the indicated number of carbon atoms such as e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-hexyl, 1,2-dimethylpropyl, 2,2-dimethylpropyl, 1,2,2-trimethylpropyl and the like. The term "C$_{1-18}$-alkyl" as used herein also includes secondary C$_{3-6}$-alkyl and tertiary C$_{4-6}$-alkyl.

The term "C$_{1-6}$-monoalkylamino" as used herein refers to an amino group wherein one of the hydrogen atoms is substituted with a straight or branched, saturated hydrocarbon chain having the indicated number of carbon atoms such as e.g. methylamino, ethylamino, propylamino, n-butylamino, sec-butylamino, isobutylamino, tert-butylamino, n-pentylamino, 2-methylbutylamino, n-hexylamino, 4-methylpentylamino, neopentylamino, n-hexylamino, 2,2-dimethylpropylamino and the like.

The term "C$_{1-6}$-dialkylamino" as used herein refers to an amino group wherein the two hydrogen atoms independently are substituted with a straight or branched, saturated hydrocarbon chain having the indicated number of carbon atoms; such as dimethylamino, N-ethyl-N-methylamino, diethylamino, dipropylamino, N-(n-butyl)-N-methylamino, di(n-pentyl)amino, and the like.

The term "acyl" as used herein refers to a monovalent substituent comprising a C$_{1-6}$-alkyl group linked through a carbonyl group; such as e.g. acetyl, propionyl, butyryl, isobutyryl, pivaloyl, valeryl, and the like.

The term "C$_{1-6}$-alkoxycarbonyl" as used herein refers to a monovalent substituent comprising a C$_{1-6}$-alkoxy group linked through a carbonyl group; such as e.g. methoxycarbonyl, carbethoxy, propoxycarbonyl, isopropoxycarbonyl, n-butoxycarbonyl, sec-butoxycarbonyl, tert-butoxycarbonyl, 3-methyl-butoxycarbonyl, n-hexoxycarbonyl and the like.

The term "3–12 membered mono- or bicyclic system" as used herein refers to a monovalent substituent of formula —NR$^2$R$^3$ or —NR$^8$R$^9$ where R$^2$ and R$^3$, or R$^8$ and R$^9$ together with the nitrogen atom form a 3–12 membered mono- or bicyclic system, in which one or more of the carbon atoms may be exchanged with nitrogen, oxygen or sulfur, such as 1-pyrrolidyl, piperidino, morpholino, thiomorpholino, 4-methylpiperazin-1-yl, 7-azabicyclo[2.2.1]heptan-7-yl, tropanyl and the like.

The term "3–6 membered saturated ring system" as used herein refers to a monovalent substituent comprising a monocyclic saturated system containing one or more hetero atoms selected from nitrogen, oxygen and sulfur and having 3–6 members and having its free valence from a carbon atom, e.g. 2-pyrrolidyl, 4-piperidyl, 3-morpholinyl, 1,4-dioxan-2-yl, 5-oxazolidinyl, 4-isoxazolidinyl, or 2-thiomorpholinyl.

The term "bicycloalkyl" as used herein refers to a monovalent substituent comprising a bicyclic structure made of 6–12 carbon atoms such as e.g. 2-norbornyl, 7-norbornyl, 2-bicyclo[2.2.2]octyl, and 9-bicyclo[3.3.1]nonanyl.

The term "aryl" as used herein refers to phenyl, 1-naphthyl, or 2-naphthyl.

The term "heteroaryl" as used herein, alone or in combination, refers to a monovalent substituent comprising a 5–6 membered monocyclic aromatic system or a 9–10 membered bicyclic aromatic system containing one or more heteroatoms selected from nitrogen, oxygen and sulfur, e.g. pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine, and purine.

The term "arylalkyl" as used herein refers to a straight or branched saturated carbon chain containing from 1 to 6 carbons substituted with an aromatic carbohydride; such as benzyl, phenethyl, 3-phenylpropyl, 1-naphtylmethyl, 2-(1-naphtyl)ethyl and the like.

The term "aryloxy" as used herein refers to phenoxy, 1-naphthyloxy or 2-naphthyloxy.

The term "arylalkoxy" as used herein refers to a C$_{1-6}$-alkoxy group substituted with an aromatic carbohydride, such as benzyloxy, phenethoxy, 3-phenylpropoxy, 1-naphthylmethoxy, 2-(1-naphtyl)ethoxy and the like.

The term "heteroarylalkyl" as used herein refers to a straight or branched saturated carbon chain containing from 1 to 6 carbons substituted with a heteroaryl group; such as (2-furyl)methyl, (3-furyl)methyl, (2-thienyl)methyl, (3-thienyl)methyl, (2-pyridyl)methyl, 1-methyl-1-(2-pyrimidyl)ethyl and the like.

The term "C$_{1-6}$-alkylsulfonyl" as used herein refers to a monovalent substituent comprising a C$_{1-6}$-alkyl group linked through a sulfonyl group such as e.g. methylsulfonyl, ethylsulfonyl, n-propylsulfonyl, isopropylsulfonyl, n-butylsulfonyl, sec-butylsulfonyl, isobutylsulfonyl, tert-butylsulfonyl, n-pentylsulfonyl, 2-methylbutylsulfonyl, 3-methylbutylsulfonyl, n-hexylsulfonyl, 4-methylpentylsulfonyl, neopentylsulfonyl, n-hexylsulfonyl and 2,2-dimethylpropylsulfonyl.

The term "C$_{1-6}$-monoalkylaminosulfonyl" as used herein refers to a monovalent substituent comprising a C$_{1-6}$-monoalkylamino group linked through a sulfonyl group such as e.g. methylaminosulfonyl, ethylaminosulfonyl, n-propylaminosulfonyl, isopropylaminosulfonyl, n-butylaminosulfonyl, sec-butylaminosulfonyl, isobutylaminosulfonyl, tert-butylaminosulfonyl, n-pentylaminosulfonyl, 2-methylbutylaminosulfonyl, 3-methylbutylaminosulfonyl, n-hexylaminosulfonyl, 4-methylpentylaminosulfonyl, neopentylaminosulfonyl, n-hexylaminosulfonyl and 2,2-dimethylpropylaminosulfonyl.

The term "C$_{1-6}$-dialkylaminosulfonyl" as used herein refers to a monovalent substituent comprising a C$_{1-6}$-dialkylamino group linked through a sulfonyl group such as dimethylaminosulfonyl, N-ethyl-N-methylaminosulfonyl, diethylaminosulfonyl, dipropylaminosulfonyl, N-(n-butyl)-N-methylaminosulfonyl, di(n-pentyl)aminosulfonyl, and the like.

The term "C$_{1-6}$-alkylsulfinyl" as used herein refers to a monovalent substituent comprising a straight or branched $C_{1-6}$-alkyl group linked through a sulfinyl group (—S(=O)—); such as e.g. methylsulfinyl, ethylsulfinyl, isopropylsulfinyl, butylsulfinyl, pentylsulfinyl, and the like.

The term "$C_{1-6}$-alkylcarbonylamino" as used herein refers to an amino group wherein one of the hydrogen atoms is substituted with an acyl group, such as e.g. acetamido, propionamido, isopropylcarbonylamino, and the like.

The term "$(C_{3-6}$-cycloalkyl$)C_{1-6}$-alkyl" as used herein, alone or in combination, refers to a straight or branched, saturated hydrocarbon chain having 1 to 6 carbon atoms and being monosubstituted with a $C_{3-6}$-cycloalkyl group, the cycloalkyl group optionally being mono- or polysubstituted with $C_{1-6}$-alkyl, halogen, hydroxy or $C_{1-6}$-alkoxy; such as e.g. cyclopropylmethyl, (1-methylcyclopropyl)methyl, 1-(cyclopropyl)ethyl, cyclopentylmethyl, cyclohexylmethyl, and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy; e.g. phenylthio, (4-methylphenyl)-thio, (2-chlorophenyl)thio, and the like.

The term "arylsulfinyl" as used herein refers to an aryl group linked through a sulfinyl group (—S(=O)—), the aryl group optionally being mono- or polysubstituted with $C_{1-6}$-alkyl, halogen, hydroxy or $C_{1-6}$-alkoxy; such as e.g. phenylsulfinyl, (4-chlorophenyl)sulfinyl, and the like.

The term "arylsulfonyl" as used herein refers to an aryl group linked through a sulfonyl group, the aryl group optionally being mono- or polysubstituted with $C_{1-6}$-alkyl, halogen, hydroxy or $C_{1-6}$-alkoxy; such as e.g. phenylsulfonyl, tosyl, and the like.

The term "$C_{1-6}$-monoalkylaminocarbonyl" as used herein refers to a monovalent substituent comprising a $C_{1-6}$-monoalkylamino group linked through a carbonyl group such as e.g. methylaminocarbonyl, ethylaminocarbonyl, n-propylaminocarbonyl, isopropylaminocarbonyl, n-butylaminocarbonyl, sec-butylaminocarbonyl, isobutylaminocarbonyl, tert-butylaminocarbonyl, n-pentylaminocarbonyl, 2-methylbutylaminocarbonyl, 3-methylbutylamino-carbonyl, n-hexylaminocarbonyl, 4-methylpentylaminocarbonyl, neopentylaminocarbonyl, n-hexylaminocarbonyl and 2-2-dimethylpropylaminocarbonyl.

The term "$C_{1-6}$-dialkylaminocarbonyl" as used herein refers to a monovalent substituent comprising a $C_{1-6}$-dialkylamino group linked through a carbonyl group such as dimethylaminocarbonyl, N-ethyl-N-methylaminocarbonyl, diethylaminocarbonyl, dipropylaminocarbonyl, N-(n-butyl)-N-methylaminocarbonyl, di(n-pentyl)aminocarbonyl, and the like.

The term "$C_{1-6}$-monoalkylaminocarbonylamino" as used herein refers to an amino group wherein one of the hydrogen atoms is substituted with a $C_{1-6}$-monoalkylaminocarbonyl group, e.g. methylaminocarbonylamino, ethylaminocarbonylamino, n-propylaminocarbonylamino, isopropylaminocarbonylamino, n-butylaminocarbonylamino, sec-butylaminocarbonylamino, isobutylaminocarbonylamino, tert-butylaminocarbonylamino, and 2-methylbutylaminocarbonylamino.

The term "$C_{1-6}$-dialkylaminocarbonylamino" as used herein refers to an amino group wherein one of the hydrogen atoms is substituted with a $C_{1-6}$-dialkylaminocarbonyl group, such as dimethylaminocarbonylamino, N-ethyl-N-methylaminocarbonylamino, diethylaminocarbonylamino, dipropylaminocarbonylamino, N-(n-butyl)-N-methylaminocarbonylamino, di(n-pentyl)aminocarbonylamino, and the like.

The term "5- or 6-membered heterocyclic system" as used herein refers to: a monocyclic unsaturated or saturated system containing one, two or three hetero atoms selected from nitrogen, oxygen and sulfur and having 5 members, e.g. pyrrole, furan, thiophene, pyrroline, dihydrofuran, dihydrothiophene, imidazole, imidazoline, pyrazole, pyrazoline, oxazole, thiazole, isoxazole, isothiazole, 1,2,3-oxadiazole, furazan, 1,2,3-triazole, 1,2,3-thiadiazole or 2,1,3-thiadiazole; an aromatic monocyclic system containing two or more nitrogen atoms and having 6 members, e.g. pyrazine, pyrimidine, pyridazine, 1,2,4-triazine, 1,2,3-triazine or tetrazine; a non-aromatic monocyclic system containing one or more hetero atoms selected from nitrogen, oxygen and sulfur and having 6 members, e.g. pyran, thiopyran, piperidine, dioxane, oxazine, isoxazine, dithiane, oxathine, thiazine, piperazine, thiadiazine, dithiazine or oxadiazine.

The term "5- or 6-membered nitrogen containing ring" as used herein refers to a monovalent substituent comprising a monocyclic unsaturated or saturated system containing one or more nitrogen atoms and having 5 or 6 members, e.g. pyrrolidinyl, pyrrolinyl, imidazolidinyl, pyrazolidinyl, pyrazolinyl, piperidyl, piperazinyl, pyrrolyl, 2H-pyrrolyl, imidazolyl, pyrazolyl, triazolyl, pyridyl, pyrazinyl, pyrimidinyl, pyridazinyl, morpholino, thiomorpholino, isothiazolyl, isoxazolyl, oxazolyl, oxadiazolyl, thiadiazolyl, 1,3-dioxolanyl, and 1,4-dioxolanyl.

In a preferred embodiment of the invention the general formula of formula I is selected from

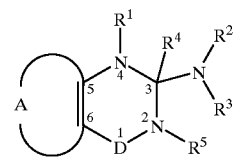

(Ia)

wherein $R^1$ and $R^5$ independently are hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen and $R^4$ is hydrogen; or $R^4$ together with $R^5$ represent one of the bonds in a double bond between the atoms 2 and 3 of formula I and $R^1$ is as defined above; or $R^4$ together with $R^1$ represent one of the bonds in a double bond between the atoms 3 and 4 of formula I and $R^5$ is as defined above;

D represents —S(=O)$_2$— or —S(=O)—.

In another preferred embodiment of the invention the general formula of formula I is selected from

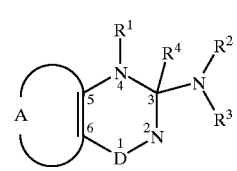

(Ib)

wherein $R^1$ is hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen and $R^4$ is hydrogen; or $R^4$ together with $R^1$ represent one of the bonds in a double bond between the atoms 3 and 4 of formula I;

D represents —S(=O)$R^7$= wherein $R^7$ is $C_{1-6}$-alkyl; or aryl or heteroaryl optionally mono- or polysubstituted with halogen, hydroxy, $C_{1-6}$-alkoxy, aryloxy, arylalkoxy, nitro, amino, $C_{1-6}$-monoalkyl- or dialkylamino, cyano, acyl or $C_{1-6}$-alkoxycarbonyl.

In another preferred embodiment of the invention the general formula of formula I is selected from

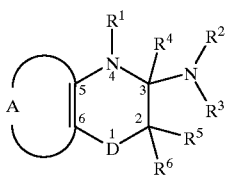

(Ic)

wherein $R^1$, $R^5$ and $R^6$ independently are hydrogen; hydroxy; $C_{1-6}$-alkoxy; or $C_{1-6}$-alkyl, $C_{3-6}$-cycloalkyl, $C_{2-6}$-alkenyl or $C_{2-6}$-alkynyl optionally mono- or polysubstituted with halogen and $R^4$ is hydrogen; or $R^4$ together with $R^5$ represent one of the bonds in a double bond between the atoms 2 and 3 of formula I and $R^1$ and $R^6$ are as defined above; or $R^4$ together with $R^1$ represent one of the bonds in a double bond between the atoms 3 and 4 of formula I and $R^5$ and $R^6$ are as defined above;

D represents —S(=O)$_2$— or S(=O).

Preferably, the general formula of formula I is (Ia).

In another preferred embodiment of the invention D is —S(=O)$_2$—.

In another preferred embodiment of the invention $R^1$ is selected from hydrogen, $C_{1-6}$-alkyl, $C_{3-6}$-cycloalkyl or $C_{2-6}$-alkenyl. Preferably $R^1$ is hydrogen or $C_{1-6}$-alkyl.

In another preferred embodiment of the invention $R^1$ together with $R^4$ represent one of the bonds in a double bond between the atoms 3 and 4 of formula I.

In another preferred embodiment of the invention $R^4$ together with $R^5$ represent one of the bonds in a double bond between the atoms 2 and 3 of formula I.

In another preferred embodiment of the invention $R^2$ is selected from hydrogen, hydroxy, $C_{1-6}$-alkyl, $C_{3-6}$-cycloalkyl or $C_{2-6}$-alkenyl. Preferably $R^2$ is hydrogen or $C_{1-6}$-alkyl.

In another preferred embodiment of the invention $R^3$ is selected from $R^8$, —O$R^8$, —N$R^8R_9$ or aryl, the aryl group optionally being substituted with $C_{1-6}$-alkyl; wherein $R^8$ is hydrogen; $C_{3-6}$-cycloalkyl; ($C_{3-6}$-cycloalkyl)$C_{1-6}$-alkyl; a 3–6-membered saturated ring system comprising one, two or three nitrogen-, oxygen- or sulfur atoms; or straight or branched $C_{1-18}$-alkyl optionally substituted with halogen, hydroxy, $C_{1-6}$-alkoxy, $C_{1-6}$-alkylthio, $C_{3-6}$-cycloalkyl or aryl; $R^9$ is hydrogen, $C_{1-6}$-alkyl or $C_{3-6}$-cycloalkyl; or $R^8$ and $R^9$ together with the nitrogen atom form a 4–6 membered ring, preferably 1-pyrrolidyl, piperidine or morpholino.

In yet another preferred embodiment of the invention $R^3$ is selected from secondary $C_{3-6}$-alkyl, tertiary $C_{4-6}$-alkyl, $C_{3-6}$-cycloalkyl or ($C_{3-6}$-cycloalkyl)methyl optionally mono- or polysubstituted with $C_{1-6}$-alkyl, halogen, hydroxy or $C_{1-6}$-alkoxy. Preferably $R^3$ is selected from isopropyl, 1-methylpropyl, 2-methylpropyl, tert-butyl, 1,1-dimethylpropyl, 1,2-dimethylpropyl, 1,2,2-trimethylpropyl, 2,3-dimethylbutyl, 1-ethylpropyl, 1-ethyl-2-methylpropyl, 1-ethyl-2,2-dimethylpropyl, 2,3,3-trimethylbutyl, 2-methylbutyl, 1,5-dimethylhexyl, 3-methylbutyl, 3-methylhexyl, cyclopropyl, 1-methylcyclopropyl, cyclobutyl, cyclopentyl, cyclohexyl, cyclopropylmethyl, 1-(cyclopropyl)ethyl cyclobutylmethyl, cyclopentylmethyl or cyclohexylmethyl.

In a further preferred embodiment of the invention $R^2$ and $R^3$ together with the nitrogen atom forms a six membered ring, optionally substituted in the 2-position with a $C_{1-6}$-alkyl group, preferably selected from methyl, ethyl or isopropyl. Preferably the six membered ring is a piperidine, piperazine, morpholine or thiomorpholine ring.

In another preferred embodiment of the invention $R^7$ is selected from $C_{1-6}$-alkyl, phenyl or pyridyl.

In another preferred embodiment of the invention A forms together with carbon atoms 5 and 6 of formula I a 5 membered heterocyclic system containing one hetero atom selected from nitrogen and sulfur, a 5 membered heterocyclic system containing two hetero atoms selected from nitrogen, oxygen and sulfur, a 6 membered aromatic heterocyclic system containing two or three nitrogen atoms, a 6 membered non-aromatic heterocyclic system containing one or two hetero atoms selected from nitrogen, oxygen and sulfur; the heterocyclic systems optionally being mono- or disubstituted with halogen; $C_{1-12}$-alkyl; $C_{3-6}$-cycloalkyl; cyano; cyanomethyl; perhalomethyl; sulfamoyl; $C_{1-6}$-alkylthio; $C_{1-6}$-alkylsulfonyl; $C_{1-6}$-alkylsulfinyl; arylthio, arylsulfinyl, arylsulfonyl, the aryl group optionally being mono- or polysubstituted with $C_{1-6}$-alkyl, halogen, hydroxy or $C_{1-6}$-alkoxy; $C_{1-6}$-alkoxycarbonyl-$C_{1-6}$-alkyl; carbamylmethyl; carboxy-$C_{1-6}$-alkyl; aryloxy; (1,2,4-oxadiazol-5-yl)- or (1,2,4-oxadiazol-3-yl)$C_{1-6}$-alkyl, the oxadiazolyl group optionally being substituted with $C_{1-6}$-alkyl or $C_{3-6}$-cycloalkyl; acyl; or a 5–6 membered nitrogen containing ring, optionally substituted with phenyl or $C_{1-6}$-alkyl.

Preferably, A forms together with carbon atoms 5 and 6 a thieno[3,2-e]- or pyrrolo[3,2-e]-ring, thiophene, imidazole, thiazole, pyrazole, isoxazole or isothiazole, a pyrazino[2,3-e]-, a pyrimido[4,5-e]-, a pyrimido[5,4-e]-, a pyridazino[4,5-e]- or a pyridazino[4,3-e]-ring, thiopyran, piperidine, dioxane, oxazine or dithiane.

Preferred compounds of the invention are:

7-Cyano-3-isopropylamino-6-methyl-4H-thieno[2,3-e]-1,2,4-thiadiazine 1,1-dioxide 7-Cyano-6-methyl-3-propylamino-4H-thieno[2,3-e]-1,2,4-thiadiazine 1,1-dioxide 6-Chloro-3-isopentylamino-4H-thieno[3,2-e]-1,2,4-thiadiazine 1,1-dioxide 6-Chloro-3-(1-methylheptyl)amino-4H-thieno[3,2-e]-1,2,4-thiadiazine 1,1-dioxide 6-Chloro-3-(1-ethylpentyl)amino-4H-thieno[3,2-e]-1,2,4-thiadiazine 1,1-dioxide 6-Chloro-3-(2-methylbutyl)amino-4H-thieno[3,2-e]-1,2,4-thiadiazine 1,1-dioxide 6-Chloro-3-(1-methylhexyl)amino-4H-thieno[3,2-e]-1,2,4-thiadiazine 1,1-dioxide 6-Chloro-3-cyclopentylamino-4H-thieno[3,2-e]-1,2,4-thiadiazine 1,1-dioxide 6-Chloro-3-cyclohexylmethylamino-4H-thieno[3,2-e]-1,2,4-thiadiazine 1,1-dioxide Ethyl 3-(6-chloro-1,4-dihydro-1,1-dioxothieno[3,2-e]-1$\lambda^6$,2,4-thiadiazin-3-ylamino)butanoate 3-(6-Chloro-1,4-dihydro-1,1-dioxothieno[3,2-e]-1$\lambda^6$,2,4-thiadiazin-3-ylamino)butanoic acid
6-Chloro-3-(3-hydroxy-1-methylpropyl)amino-4H-thieno[3,2-e]-1,2,4-thiadiazine 1,1-dioxide
(R)-6-Chloro-3-(1-phenylethyl)amino-4H-thieno[3,2-e]-1,2,4-thiadiazine 1,1-dioxide
(S)-3-sec-Butylamino-6-chloro-4H-thieno[3,2-e]-1,2,4-thiadiazine 1,1-dioxide
6-Chloro-3-isopropylamino-4H-thieno[2,3-e]-1,2,4-thiadiazine 1,1-dioxide
6-Chloro-3-cyclopentylamino-4H-thieno[2,3-e]-1,2,4-thiadiazine 1,1-dioxide
6-Bromo-3-isopropylamino-4H-thieno[3,2-e]-1,2,4-thiadiazine 1,1-dioxide
3-Isopropylamino-4H-thieno[3,2-e]-1,2,4-thiadiazine 1,1-dioxide
6-Fluoro-3-isopropylamino-4H-thieno[3,2-e]-1,2,4-thiadiazine 1,1-dioxide
3-Cyclobutylamino-5,6-dimethyl-4H-thieno[3,2-e]-1,2,4-thiadiazine 1,1-dioxide
3-Cyclopentylamino-5,6-dimethyl-4H-thieno[3,2-e]-1,2,4-thiadiazine 1,1-dioxide
3-Isopropylamino-6,7-dimethyl-4H-thieno[2,3-e]-1,2,4-thiadiazine 1,1-dioxide
3-Cyclobutylamino-6,7-dimethyl-4-H-thieno[2,3-e]-1,2,4-thiadiazine 1,1-dioxide
3-Cyclopentylamino-6,7-dimethyl-4H-thieno[2,3-e]-1,2,4-thiadiazine 1,1-dioxide
5-Chloro-3-isopropylamino-4H-thieno[3,2-e]-1,2,4-thiadiazine 1,1-dioxide
5-Chloro-3-propylamino-4H-thieno[3,2-e]-1,2,4-thiadiazine 1,1-dioxide
5-Chloro-3-cyclopentylamino-4H-thieno[3,2-e]-1,2,4-thiadiazine 1,1-dioxide
5-Chloro-6-methyl-3-isopropylamino-4H-thieno[3,2-e]-1,2,4-thiadiazine 1,1-dioxide
6-chloro-3-isopropylamino-5-methyl-4H-thieno[3,2-e]-1,2,4-thiadiazine 1,1-dioxide
6-chloro-3-cyclopentylamino-5-methyl-4H-thieno[3,2-e]-1,2,4-thiadiazine 1,1-dioxide
6-Fluoro-3-propylamino-4H-thieno[3,2-e]-1,2,4-thiadiazine 1,1-dioxide
6-Fluoro-3-cyclopentylamino-4H-thieno[3,2-e]- 1,2,4-thiadiazine 1,1-dioxide
5-Fluoro-3-propylamino-4H-thieno[3,2-e]-1,2,4-thiadiazine 1,1-dioxide
5-Fluoro-3-isopropylamino-4H-thieno[3,2-e]-1,2,4-thiadiazine 1,1-dioxide.
3-Isopropylamino-7-methyl-4H-thieno[2,3-e]-1,2,4-thiadiazine 1,1-dioxide
6-Chloro-3-cyclobutylamino-4H-thieno[3,2-e]-1,2,4-thiadiazine 1,1-dioxide
6-Chloro-3-(2-hydroxyethyl)amino-4H-thieno[3,2-e]-1,2,4-thiadiazine 1,1-dioxide
(±)-3-exo-Bicyclo[2.2.]hept-2-ylamino-6-chloro-4H-thieno[3,2-e]-1,2,4-thiadiazine 1,1-dioxide
(R)-6-Chloro-3-(2-hydroxypropyl)amino-4H-thieno[3,2-e]-1,2,4-thiadiazine 1,1-dioxide
6-Bromo-3-isopropylamino-4H-thieno[3,2-e]-1,2,4-thiadiazine 1,1-dioxide
5,6-Dibromo-3-isopropylamino-4H-thieno[3,2-e]-1,2,4-thiadiazine 1,1-dioxide6-Chloro-3-cyclohexylamino-4H-thieno[3,2-e]-1,2,4-thiadiazine 1,1-dioxide
6-Chloro-3-(furan-2-ylmethyl)amino-4H-thieno[3,2-e]-1,2,4-thiadiazine 1,1-dioxide
6-Chloro-3-(1-ethylpropyl)amino-4H-thieno[3,2-e]-1,2,4-thiadiazine 1,1-dioxide
6-Bromo-3-cyclopentylamino-4H-thieno[3,2-e]-1,2,4-thiadiazine 1,1-dioxide
6-Chloro-3-(2-methylallyl)amino-4H-thieno[3,2-e]-1,2,4-thiadiazine 1,1-dioxide or
6-Cyano-3-isopropylamino-4H-thieno[3,2-e]-1,2,4-thiadiazine 1,1-dioxide.

The compounds of the present invention interact with the potassium channels and hence act as openers or blockers of the ATP-regulated potassium channels, which make them useful in the treatment of various diseases of the cardiovascular system, e.g. cerebral ischemia, hypertension, ischemic heart diseases, angina pectoris and coronary heart diseases; the pulmonary system; the gastrointestinal system; the central nervous system and the endocrinological system.

Since some $K_{ATP}$-openers are able to antagonize vasospasms in basilar or cerebral arteries the compounds of the present invention can be used for the treatment of vasospastic disorders such as subarachnoid hemorrhage and migraine.

The compounds of the present invention may also be used for the treatment of diseases associated with decreased skeletal muscle blood flow such as Raynauds disease and intermittent claudication.

Further, the compounds of the invention may be used for the treatment of chronic airway diseases, including asthma, and for treatment of detrusor muscle instability secondary to bladder outflow obstruction and therefore for kidney stones by aiding their passage along the urethra.

The present compounds could also be used for treatment of conditions associated with disturbances in gastrointestinal mobility such as irritable bowel syndrome. Additionally these compounds can be used for the treatment of premature labour and dysmenorrhea.

Potassium channel openers hyperpolarize neurons and inhibit neurotransmitter release and it is expected that such compounds can be used for the treatment of various diseases of the central nervous system, e.g. epilepsia, ischemia and neurodegenerative diseases, and for the management of pain.

Further, potassium channel openers promote hairgrowth, therefore, the compounds of the present invention can be used for the treatment of baldness.

Potassium channel openers also relax urinary bladder smooth muscle, thus, the compounds of the present invention can be used for the treatment of urinary incontinence.

In diseases such as nesidioblastosis and insulinoma in which a hypersecretion of insulin causes severe hypoglycemia the compounds of the present invention can be used to reduce insulin secretion. In obesity hyperinsulinemia and insulin resistance is very frequently encountered. This condition could lead to the development of noninsulin dependent diabetes (NIDDM). It is expected that potassium channel openers, and hence the compounds of the present invention, can be used for reducing the hyperinsulinemia and thereby prevent diabetes and reduce obesity. In overt NIDDM treatment of hyperinsulinemia with potassium channel openers, and hence the present compounds, can be of benefit in restoring glucose sensitivity and normal insulin secretions.

In early cases of insulin dependent diabetes (IDDM) or in prediabetic cases, potassium channel openers and hence the present compounds can be used to induce pancreatic cell rest which may prevent the progression of the autoimmune disease.

The potassium channel openers of the present invention can be administered in combination with an immunosuppressant or with an agent like nicotinamide, which will reduce autoimmune degeneration of beta-cells.

Combining beta-cell rest with a treatment protecting the beta-cells against cytokine mediated beta-cell impairment/cytotoxicity is another aspect of this invention. Insulin requiring or Type 1 diabetes (IDDM) as well as late onset IDDM (also known as type 1.5. e.g. non-insulin-requiring Type 2 (NIIDM) patients with autoreactivity against beta-cell epitopes that later turns insulin requiring) have circulating autoreactive monocytes/lymphocytes that homes to the islets/beta-cells and releases their cytokines. Some of these cytokines (e.g. interleukin-1b (IL-1b), tumour necrosis factor a (TNFa) and interferon g (IFNg)) are specifically toxic to the beta-cells, e.g. through the induction of nitric oxide (NO) and other free radicals. Inhibition of this cytotoxicity, e.g. by coadministring nicotinamide (NA), a derivative hereof or other cytokine protective compounds to the prediabetic/diabetic patients treated with the PCO compound is an example of this aspect. Nicotinamide belongs to the B-vitamin family and is derived from nicotinic acid by amidation of the carboxyl group. It processes none of nicotine's pharmacological properties. NA is converted into NAD+, which acts as a coenzyme for proteins involved in tissue respiration. NA has been proposed to influence several of the putative intracellular molecular events following immune attack on the beta-cells. Animal experiments and early non-blinded experiments in humans have indicated a protective role of this compound against IDDM as well as in cytokine/immune mediated beta-cell destruction. Yet another aspect of this application concerns the use of a PCO compound alone or in combination with the inhibitor of cytokine/immune mediated beta-cell impairment, in transplantation, e.g. islet transplantation into diabetes patients. The use of one or both of these treatments may reduce the risk of rejection of the transplanted islets/beta-cells/engineered beta-cells/pancreas.

Compounds of the present invention which act as blockers of $K_{ATP}$-channels can be used for the treatment of NIDDM.

Preferably, the compounds of the present invention may be used for treatment or prevention of diseases of the endocrinological system such as hyperinsulinemia and diabetes.

Accordingly, in another aspect the invention relates to a compound of the general formula I or a pharmaceutically acceptable acid addition salt thereof for use as a therapeutically acceptable substance, preferably for use as a therapeutically acceptable substance in the treatment of hyperinsulinemia and treatment or prevention of diabetes.

Furthermore, the invention also relates to the use of the inventive compounds of formula I as medicaments useful for treating hyperinsulinemia and treating or preventing diabetes.

In yet another aspect, the present invention relates to methods of preparing the above mentioned compounds. The methods comprises:

a) reacting a compound of formula II:

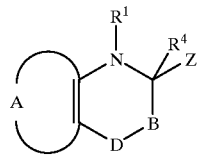

(II)

wherein A, B, D, $R^1$ and $R^4$ are as defined above and Z is a leaving group such as alkoxy, alkylthio, halogen, preferentially chloro, bromo, iodo, trimethylamino, or methylsulfonyl with a compound of formula III:

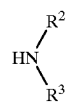

(III)

wherein $R^2$ and $R^3$ are defined above to form a compound of the general formula I;

b) reacting a compound of formula IV:

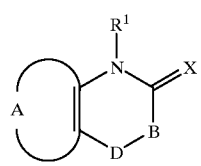

(IV)

wherein $R^1$ is hydrogen and A, B, D and X are as defined above, or B is NH and $R^1$, A, D and X are as defined above, with the compound of formula III, or a suitable salt thereof in the presence of $P_2O_5$ and a high boiling tertiary amine or a suitable salt thereof, to form a compound of the general formula I;

c) reacting a compound of the formula IV:

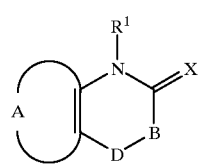

(IV)

wherein $R^1$ is hydrogen and A, B. D and X are as defined above or B is NH and $R^1$, A, D and X are as defined above, with a compound of the formula III, or a suitable salt thereof in the presence of titanium tetrachloride and a solvent with which it may form a complex, like e.g. tetrahydrofuran, or a mixture of toluene and anisole, to form a compound of the general formula I;

d) reacting a compound of formula V

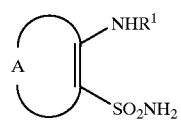

(V)

wherein $R^1$ and A are as defined above, with a compound of formula VI

$R^3NCO$ (VI)

wherein $R^3$ is as defined above, to form a compound of the general formula I wherein D is $SO_2$, B is >$NR^5$, $R^2$ is H, and $R^4$ and $R^5$ together form a bond;

e) reacting a compound of the formula V

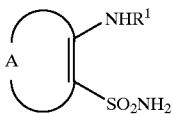
(V)

wherein $R^1$ and A are as defined above, with a compound of formula VII $R^3NHC(=O)Cl$ (VII)

wherein $R^3$ is as defined, to form a compound of the general formula I wherein D is $SO_2$, B is >$NR^5$, $R^2$ is H, and $R^4$ and $R^5$ together form a bond;

f) reacting a compound of the formula V

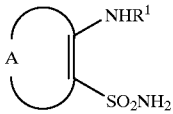
(V)

wherein $R^1$ and A are defined as above, with a compound of formula VIII

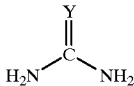
(VIII)

wherein Y is NH or S, or a suitable salt thereof, to form a compound of the general formula I, wherein D is $SO_2$, B is >$NR^5$, $R^4$ and $R^5$ together form a bond, and $R^2$ and $R^3$ are H;

g) reacting in the presence of a base a compound of formula IX

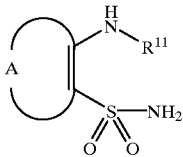
(IX)

or a suitable salt thereof, wherein $R^{11}$ is $R^1$ or EtOC(=O), wherein $R^1$ and A are defined as above, with a compound of formula X $R^3N=C=S$ (X)

wherein $R^3$ is as defined above, to form an adduct which may have either of the two structures XI or XII or be a mixture of the two

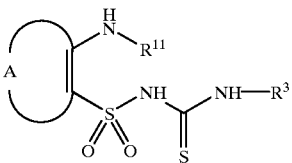
(XI)

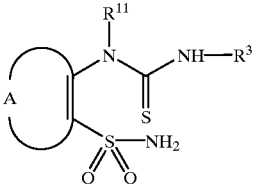
(XII)

either of which by ring-closure, e.g. by treatment with phosgene in a suitable solvent, forms a compound of the general formula I, if $R^{11}$ is $R^1$, wherein D is $S(=O)_2$, B is >$NR^5$, $R^2$ is H, and $R^4$ and $R^5$ together form a bond, and a compound of the general formula XIII if $R^{11}$ is EtOC(=O);

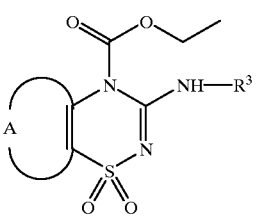
(XIII)

h) hydrolyzing and subsequently decarboxylating a compound of the general formula XIII

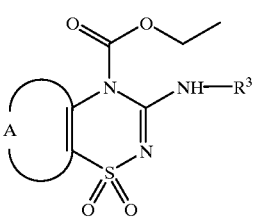
(XIII)

to form a compound of the general formula I, wherein D is $S(=O)_2$, B is >$NR^5$, $R^1$ and $R^2$ are H, and $R^4$ and $R^5$ together form a bond, e.g. by heating the starting compound in aqueous base.

The starting materials are either known compounds or compounds which may be prepared in analogy with the preparation of known compounds or in analogy with known methods as described by e.g Huang B.-S., et al., J. Med. Chem., 23, 575–7 (1980), Ofitserov V. I. et al., Khim. Geterotsikl. Soedin., 1119–22 (russ.) (1976), Topliss J. G., U.S. Pat. No. 3,641,017 (1972), Kotovskaya S. K. et al., Khim.-Farm. Zh., 13, 54–57 (russ.) (1979), Meyer R. F., J. Heterocycl. Chem., 6, 407–408 (1969) and Hattori M., Yoneda M., and Goto M., Bull. Chem. Soc. Jap., 46, 1890–1 (1973), Williams T. R. and Cram D. J., J. Org. Chem., 38, 20–26 (1973), Barnes A. C., Kennewell P. D. and Taylor J. B., J. Chem. Soc. Chem. Commun., 1973, 776–777, Stoss and Satzinger, Chem. Ber., 109, 2097 (1976) Kresze G., Hatjiissaak A., Phosphorus Sulfur, 29, 41–47 (1987), Dillard R. D., Yen T. T., Stark P., Pavey D. E., J. Med. Chem., 23, 717–722 (1980).

Pharmacological Methods

The ability of the compounds to interact with potassium channels can be determined by various methods. When patch-clamp techniques (Hamill O. P., Marty A., Neher E., Sakmann B. and Sigworth F. J., *Plügers Arch.*, 391, 85–100 (1981)) are used the ionic current through a single channel of a cell can be recorded.

The activity of the compounds as potassium channel openers can also be measured as relaxation of rat aorta rings according to the following procedure:

A section of rat thoracic aorta between the aortic arch and the diaphragm was dissected out and mounted as ring preparations as described by Taylor P. D. et al, *Brit J. Pharmacol*, 111, 42–48 (1994).

After a 45 min. equilibration period under a tension of 2 g, the preparations were contracted to achieve 80% of the maximum response using the required concentration of phenylephrine. When the phenylephrine response reached a plateau, potential vasodilatory agents were added cumulatively to the bath in small volumes using half log molar increments at 2 min intervals. Relaxation was expressed at the percentage of the contracted tension. The potency of a compound was expressed as the concentration required to evoke a 50% relaxation of the tissue.

| Relaxation of rat aorta rings | |
|---|---|
| Example | EC50 micro M |
| 4 | 2.8 |
| 6 | 20.5 |

In the pancreatic b-cell the opening of the $K_{ATP}$-channels can be determined by measuring the subsequent change in the concentration of cytoplasmic free $Ca^{2+}$ concentration according to the method of Arkhammar P. et al., *J. Biol. Chem.*, 262, 5448–5454 (1987).

$^{86}Rb^+$ Efflux from a β-cell line

The RIN 5F cell line was grown in RPMI 1640 with Glutamax I, supplemented with 10% fetal calf serum (from GibcoBRL, Scotland, UK) and maintained in an atmosphere of 5% $CO_2$/95% air at 37° C. The cells were detached with a Trypsin-EDTA solution (from GibcoBRL, Scotland, UK), resuspended in medium, added 1 mCi/ml $^{86}Rb^+$ and replated into microtiter plates (96 well cluster 3596, sterile, from Costar Corporation, MA, USA) at a density of 50000 cells/well in 100 µl/well, and grown 24 hours before use in assay.

The plates were washed 4 times with Ringer buffer (150 mM NaCl, 10 mM Hepes, 3.0 mM KCl, 1.0 mM $CaCl_2$, 20 mM Sucrose, pH 7.1). Eighty µl Ringer buffer and 1 µl control- or test compound dissolved in DMSO was added. After incubation 1 h at room temperature with a lid, 50 µl of the supernatant was transferred to PicoPlates (Packard Instrument Company, CT, USA) and 100 µl MicroScint40 (Packard Instrument Company, CT, USA) added. The plates were counted in TopCount (Packard Instrument Company, CT, USA) for 1 min/well at the $^{32}P$ program.

The calculation of $EC_{50}$ and $E_{max}$ was done by SlideWrite (Advanced Graphics Software, Inc., CA, USA) using a four parameter logistic curve: $y=(a-d)/(1+(x/c)^b)+d$, where a=the activity estimated at concentration zero, b=a slope factor, c=the concentration at the middle of the curve and, d=the activity estimated at infinite concentration. $EC_{50}$=c and $E_{max}$=d, when the curve is turned of at infinite concentrations.

| Increased Rb-efflux in rin 5F cells | |
|---|---|
| Example | EC50 micro M |
| 4 | 5.5 |
| 6 | 31 |

The compounds according to the invention are effective over a wide dose range. In general satisfactory results are obtained with dosages from about 0.05 to about 1000 mg, preferably from about 0.1 to about 500 mg, per day. A most preferable dosage is about 1 mg to about 100 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intramuscular or intranasal, the oral route being preferred.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 1 to about 100 mg in a pharmaceutically acceptable carrier per unit dosage.

A typical tablet, appropriate for use in this method, may be prepared by conventional tabletting techniques and contains:

| Active compound | 5.0 mg |
|---|---|
| Lactosum | 67.8 mg Ph. Eur. |
| Avicel ® | 31.4 mg |
| Amberlite ® | 1.0 mg |
| Magnesii stearas | 0.25 mg Ph. Eur. |

EXAMPLES

The process of preparing the compounds of formula I is further illustrated in the following examples which, however, are not to be construed as limiting.

Example 1

7-Cyano-3-isopropylamino-6-methyl-4H-thieno[2,3-e]-1,2,4-thiadiazine1,1-dioxide a) 4-Cyano-2-hydrazinocarbonyl-5-methyl-thiophene-3-sulfonamide Methyl 4-cyano-5-methyl-3-sulfamoyl-thiophene-2-carboxylate (2.9 g), prepared from methyl 3-amino-4-cyano-5-methyl-thiophene-2-carboxylate in analogy with known procedures, e.g. F. Junquera et al., Eur.J.Med.Chem. 23, 329 (1988), was suspended in 10 ml of ethanol. Hydrazine monohydrate (2 ml) was added and the mixture was stirred for 1 h at room temperature and then evaporated. The oily residue (3.3 g) was triturated with 10 ml of water and the precipitating crystals were collected by filtration, washed with water and dried to give the title compoundas yellow crystals (yield 1.62 g); m.p. 186–91° C.; $^1$H-NMR (DMSO-d$_6$), δ(ppm): 7.25 (br, 5H, NH/NH$_2$), 2.51 (s, 3H, CH$_3$).

b) 4-Cyano-5-methyl-3-sulfamoyl-thiophene-2-carbonyl azide

A solution of sodium nitrite (0.47 g) in 5 ml of water was added dropwise to a stirred solution of 4-cyano-2-hydrazinocarbonyl-5-methyl-thiophene-3-sulfonamide (1.6 g) in 38 ml of 1 M hydrochloric acid at 0° C. The resulting mixture was stirred for 30 min at 0° C. and then filtered. The filter cake was washed with water and dried in vacuum to give 1.35 g of the title compound; $^1$H-NMR (DMSO-d$_6$), δ(ppm): 7.75 (br, 1H, NH$_2$), 2.75 (s, 1H, CH$_3$).

c) 4-Cyano-2-ethoxycarbonylamino-5-methyl-thiophene-3-sulfonamide 4-cyano-5-methyl-3-sulfamoyl-thiophene-2-carbonyl azide (1.35 g) was added in small portions over 5 min to 50 ml of abs. ethanol at reflux temperature. The resulting solution was refluxed for 5 min and then evaporated. The residue crystallized when triturated with 20 ml of ethyl acetate. The crystals were filtered off, rinsed with etyl acetate and dried to give the title compound; $^1$H-NMR (DMSO-d$_6$), δ(ppm): 9.45 (s, 1H, NH), 7.82 (br, 2H, NH$_2$), 4.23 (q, 2H, CH$_2$), 2.51 (s, 3H, CH$_3$), 1.25 (t, 3H, CH$_3$).

d) N-(4-Cyano-2-ethoxycarbonylamino-5-methyl-3-thienylsulfonyl)-N'-isopropylthiourea A mixture of 4-cyano-2-ethoxycarbonylamino-5-methyl-thiophene-3-sulfonamide (0.50 g), potassium carbonate (0.36 g) and isopropyl isothiocyanate (300 μl) in 10 ml of dry acetone was heated at 55° C. for 18 h and then evaporated to dryness. The residue was dissolved in 10 ml of water, and pH was adjusted to 2 by dropwise addition of 1M hydrochloric acid. The precipitate was filtered off, rinsed with a small amount of water and dried to give 0.34 g of the title compound; m.p. 169–171° C.

e) Ethyl 7-cyano-3-isopropylamino-6-methyl-4H-thieno[2,3-e]-1,2,4-thiadiazine-4-carboxylate 1,1-dioxide To a stirred solution of N-(4-cyano-2-ethoxycarbonylamino-5-methyl-3-thienylsulfonyl)-N'-isopropylthiourea (0.3 g) and triethylamine (320 μl) in 10 ml of dry THF at 0° C. was added 750 μl of a 20% solution of phosgene in toluene. The mixture was stirred at 0° C. for 1 h and then evaporated to dryness. The residue was triturated with 10 ml of water, filtered off, rinsed on the filter with water and dried to give 0.24 g of crude title compound; m.p. 116–119° C. The product was used for the next step without purification.

f) 7-Cyano-3-isopropylamino-6-methyl-4H-thieno[2,3-e]-1,2,4-thiadiazine 1,1-dioxide A mixture of ethyl 7-cyano-3-isopropylamino-6-methyl-4H-thieno[2,3-e]-1,2,4-thiadiazine-4-carboxylate 1,1-dioxide (0.15 g) and 5 ml of 1 M aqueous sodium hydroxide was stirred at room temperature for 1 h. Then the mixture was filtered and pH was adjusted to 1–2 by dropwise addition of 4M hydrochloric acid. After stirring for 30 min the precipitate was filtered off, rinsed with a small amount of water and dried to give the title compound; m.p. m.p. 235–238° C.; $^1$H-NMR (DMSO-d$_6$) δ(ppm): 11.35 (s, 1H, NH), 7.55 (br d, 1H, NH), 3.98–3.77 (m, 1H, CH), 2.50 (s, 1H, CH$_3$), 1.15 (d, 6H, CH$_3$).

Example 2

7-Cyano-6-methyl-3-propylamino-4H-thieno[2,3-e]-1,2,4-thiadiazine 1,1-dioxide a) N-(4-Cyano-2-ethoxycarbonylamino-5-methyl-3-thienylsulfonyl)-N'-propylthiourea The title compound was prepared from 4-cyano-2-ethoxycarbonylamino-5-methyl-thiophene-3-sulfonamide and propyl isothiocyanate in analogy with the synthesis described in Example 1-d; m.p. 167–168° C.

b) Ethyl 7-cyano-6-methyl-3-propylamino4H-thieno[2,3-e]-1,2,4-thiadiazine-4-carboxylate 1,1-dioxide The title compound was prepared by ring closure of N-(4-cyano-2-ethoxycarbonylamino-5-methyl-3-thienylsulfonyl)-N'-propylthiourea in analogy with the synthesis described in Example 1-e; m.p. 175–179° C.

c) 7-Cyano-6-methyl-3-propylamino-4H-thieno[2,3-e]-1,2,4-thiadiazine 1,1-dioxide The title compound was prepared by hydrolysis and subsequent decarboxylation of ethyl 7-cyano-6-methyl-3-propylamino-4H-thieno[2,3-e]-1,2,4-thiadiazine-4-carboxylate 1,1-dioxide in analogy with the synthesis described in Example 1-f; m.p. 293–98° C.; $^1$H-NMR (DMSO-d$_6$), δ(ppm): 11.6 (s, 1H, NH), 7.65 (br, 1H, NH), 3.14 (dd, 2H, CH$_2$), 2.58 (s, 1H, CH$_3$), 1.65–1.4 (m, 2H, CH$_2$), 0.89 (t, 3H, CH$_3$).

Example 3

6-Chloro-3-(3-methylbutyl)amino-4H-thieno[3,2-e]-1,2,4-thiadiazine 1,1-dioxide a) N-(3-Amino-5-chloro-2-thienylsulfonyl)-N'-(3-methylbutyl)thiourea

Potassium tert-butoxide (0.49 g, 4.4 mmol) was added to a solution of 3-amino-5-chlorothiophene-2-sulfonamide hydrochloride (0.5 g, 2.0 mmol) in dry N,N-dimethylformamide (5 ml) with stirring on an ice bath. After 10 min, 3-methylbutyl isothiocyanate (0.31 g, 2.4 mmol) was added dropwise to the resulting suspension, and the mixture was stirred for 3.5 h at 0 to 20° C. Most of the solvent was evaporated at 40° C., and the residue was taken up in 25 ml of water, treated with decolourising charcoal, and filtered. Acidification of the filtrate with acetic acid to pH 3–4 and filtration afforded 0.21 g (29%) of the title compound; mp 114–115° C. decomp., $^1$H-NMR (DMSO-$d_6$): δ0.85 (d, 6H, 2×CH$_3$), 1.40 (q, 2H, CH$_2$), 1.50 (m, 1H, CH), 3.45 (q, 2H, CH$_2$), 6.45 (br, 2H, NH$_2$), 6.65 (s, 1H, H4), 8.30 (br t, 1H, NH), 11.3 (br s, 1H).

b) 6-Chloro-3-(3-methylbutyl)amino-4H-thieno[3,2-e]-1,2,4-thiadiazine 1,1-dioxide Phosgene (0.242 ml, 20% in toluene) was added dropwise to a solution of N-(3-amino-5-chloro-2-thienylsulfonyl)-N'-(3-methylbutyl)thiourea (0.153 g, 0.42 mmol) and dry triethylamine (0.118 ml, 0.85 mmol) in dry tetrahydrofuran (3 ml) with stirring at 0° C. The mixture was stirred for 2 h at 0° C., and evaporated to dryness. Crystallisation was obtained from ethyl acetate, and the precipitate was isolated by filtration, washed with water and dried affording 38 mg (27%) of the title compound. mp 230–231.5° C., $^1$H-NMR (DMSO-$d_6$): δ0.90 (d, 6H, 2×CH$_3$), 1.40 (q, 2H, CH$_2$),1.60 (m, 1H, CH), 3.20 (q, 2H, CH$_2$), 7.05 (s, 1H, H-5), 7.25 (br s, 1H, NH), 10.95 (s, 1H, NH). MS: M/e 307(M+).

Example 4

6-Chloro-3-(1-methylheptyl)amino-4H-thieno[3,2-e]-1,2,4-thiadiazine 1,1-dioxide cl a) N-(3-Amino-5-chloro-2-thienylsulfonyl)-N'-(1-methylheptyl)thiourea The title compound was prepared from 3-amino-5-chlorothiophene-2-sulfonamide hydrochloride and 1-methylheptyl isothiocyanate by a procedure analogous to the procedure described in example 3-a; a syrup was obtained (yield 29%), $^1$H-NMR (DMSO-$d_6$): δ0.90 (t, 3H, CH$_3$), 1.10 (d, 3H, CH$_3$), 1.25 (m, 8H), 1.47 (m, 2H, CH$_2$), 4.25 (p, 1H, CH), 6.5 (br s, 2H, NH$_2$), 6.65 (s, 1H, H-4), 7.95 (br, 1H, NH), 11.2 (br s, 1H).

b) 6-Chloro-3-(1-methylheptyl)amino-4H-thieno[3,2-e]-1,2,4-thiadiazine 1,1-dioxide The title compound was prepared from N-(3-amino-5-chloro-2-thienylsulfonyl)-N'-(1-methylheptyl)thiourea by a procedure analogous to the procedure described in example 3-b (yield 71%); mp 179–181° C., $^1$H-NMR (DMSO-$d_6$): δ0.85 (t, 3H, CH$_3$), 1.15 (d, 3H, CH$_3$), 1.30 (m, 8H), 1.45 (m, 2H, CH$_2$), 3.75 (p, 1H, CH), 7.05 (s, 1H, H-5), 7.10 (br s, 1H, NH), 10.65 (s, 1H, NH). MS: M/e 349 (M+).

Example 5

6-Chloro-3-(1-ethylpentyl)amino4H-thieno[3,2-e]-1,2,4-thiadiazine-1,1-dioxide a) N-(3-Amino-5-chloro-2-thienylsulfonyl)-N'-(1-ethylpentyl)thiourea

The title compound was prepared from 3-amino-5-chlorothiophene-2-sulfonamide hydrochloride and 1-ethylpentyl isothiocyanate by a procedure analogous to the procedure described in example 3-a; a syrup was obtained (yield 36%), $^1$H-NMR (DMSO-$d_6$): δ0.8 (2 q, 6H, 2×CH$_3$), 1.2 (m, 4H), 1.5 (m, 4H), 4.20 (sextet, 1H, CH), 6.55 (br, 2H, NH$_2$), 6.65 (s, 1H, H4), 7.85 (br d, 1H, NH), 11.3 (br s, 1H, NH).

b) 6-Chloro-3-(1-ethylpentyl)amino-4H-thieno[3,2-e]-1,2,4-thiadiazine 1,1-dioxide The title compound was prepared from N-(3-amino-5-chloro-2-thienylsulfonyl)-N'-(1-ethylpentyl)thiourea by a procedure analogous to the procedure described in example 3-b (yield 35%); mp 165–167.5° C., $^1$H-NMR (DMSO-$d_6$): δ0.85 (2 q, 6H, 2×CH$_3$), 1.25 (m, 4H), 1.45 (m, 4H), 3.65 (m, 1H, CH), 7.0 (br, 1H, NH), 7.05 (s, 1H, H-5), 10.65 (br s, 1H, NH). MS: M/e 335 (M+).

Example 6

6-Chloro-3-(2-methylbutyl)amino-4H-thieno[3,2-e]-1,2,4-thiadiazine 1,1-dioxide a) N-(3-Amino-5-chloro-2-thienylsulfonyl)-N'-(2-methylbutyl)thiourea

The title compound was prepared from 3-amino-5-chlorothiophene-2-sulfonamide hydrochloride and 2-methylbutyl isothiocyanate by a procedure analogous to the procedure described in example 3-a (yield 28%); mp 116.5–118° C., $^1$H-NMR (DMSO-$d_6$): δ0.8 (2 d, 6H, 2×CH$_3$), 1.10 (m, 1H), 1.30 (m, 1H), 1.65 (m, 1H), 3.40 (m, 2H+HDO, CH$_2$), 6.45 (br, 2H, NH$_2$), 6.65 (s, 1H, H-4), 8.25 (br t, 1H, NH), 11.3 (br s, 1H).

b) 6-Chloro-3-(2-methylbutyl)amino-4H-thieno[3,2-e]-1,2,4-thiadiazine 1,1-dioxide The title compound was prepared from N-(3-amino-5-chloro-2-thienylsulfonyl)-N'-(2-methylbutyl)thiourea by a procedure analogous to the procedure described in example 3-b (yield 49%); mp 232–234° C., $^1$H-NMR (DMSO-$d_6$): δ0.85 (2 d, 6H, 2×CH$_3$), 1.15 (m, 1H), 1.40 (m, 1H), 1.60 (m, 1H), 3.10 (m, 2H, CH$_2$), 7.05 (s, 1H, H-5), 7.25 (br, 1H, NH), 10.85 (br s, 1H, NH). MS: M/e 307 (M+).

Analysis: calc. For $C_{10}H_{14}ClN_3O_2S_2$ C, 39.02; H, 4.58; N, 13.65; found C, 38.98; H, 4.72; N, 13.40.

Example 7

6-Chloro-3-(1-methylhexyl)amino-4H-thieno[3,2-e]-1,2,4-thiadiazine 1,1-dioxide a) N-(3-Amino-5-chloro-2-thienylsulfonyl)-N'-(1-methylhexyl)thiourea

The title compound was prepared from 3-amino-5-chlorothiophene-2-sulfonamide hydrochloride and 1-methylhexyl isothiocyanate by a procedure analogous to the procedure described in example 3-a; a syrup was obtained (yield 43%), $^1$H-NMR (DMSO-$d_6$): δ0.85 (t, 3H, CH$_3$), 1.10 (d, 3H, CH$_3$), 1.25 (m, 6H), 1.45 (m, 2H), 4.25 (m, 1H, CH), 6.50 (br, 2H, NH$_2$), 6.65 (s, 1H, H-4), 7.93 (br, 1H, NH), 11.3 (br s, 1H, NH).

b) 6-Chloro-3-(1-methylhexyl)amino-4H-thieno[3,2-e]-1,2,4-thiadiazine 1,1-dioxide The title compound was prepared from N-(3-amino-5-chloro-2-thienylsulfonyl)-N'-(1-methylhexyl)thiourea by a procedure analogous to the procedure described in example 3-b (yield 63%); mp 158–162° C., $^1$H-NMR (DMSO-d$_6$): δ0.85 (t, 3H, CH$_3$), 1.15 (d, 3H, CH$_3$), 1.25 (m, 6H), 1.45 (m, 2H), 3.75 (m, 1H, CH), 7.05 (s, 1H, H-5), 7.15 (br s, 1H, NH), 10.75 (br s, 1H, NH). MS: M/e 335 (M+).

Example 8

6-Chloro-3-(cyclopentyl)amino-4H-thieno[3,2-e]-1, 2,4-thiadiazine 1,1-dioxide a) N-(3-Amino-5-chloro-2-thienylsulfonyl)-N'-cyclopentylthiourea The title compound was prepared from 3-amino-5-chlorothiophene-2-sulfonamide hydrochloride and cyclopentyl isothiocyanate by a procedure analogous to the procedure described in example 3-a (yield 46%); $^1$H-NMR (DMSO-d$_6$): δ1.30–1.70 (m, 6H), 1.90 (m, 2H), 4.40 (sextet, 1H, CH), 6.55 (br, 2H, NH$_2$), 6.65 (s, 1H, H-4), 8.15 (br d, 1H, NH), 11.2 (br s, 1H, NH).

b) 6-Chloro-3-(cyclopentyl)amino-4H-thieno[3,2-e]-1,2,4-thiadiazine 1,1-dioxide

The title compound was prepared from N-(3-amino-5-chloro-2-thienylsulfonyl)-N'-cyclopentylthiourea by a procedure analogous to the procedure described in example 3-b (yield 57%); mp 291–292° C., $^1$H-NMR (DMSO-d$_6$): δ1.40–1.70 (m, 6H, CH$_3$), 1.90 (m, 2H), 3.95 (sextet, 1H, CH), 7.05 (s, 1H, H-5), 7.3 (br, 1H, NH), 10.70 (br s, 1H, NH). MS: M/e 305 (M+).

Example 9

6-Chloro-3-(cyclohexylmethyl)amino-4H-thieno[3,2-e]-1,2,4-thiadiazine 1,1-dioxide a) N-(3-Amino-5-chloro-2-thienylsulfonyl)-N'-cyclohexylmethylthiourea The title compound was prepared from 3-amino-5-chlorothiophene-2-sulfonamide hydrochloride and cyclohexylmethyl isothiocyanate by a procedure analogous to the procedure described in example 3-a; a syrup was obtained (yield 8%), $^1$H-NMR (DMSO-d$_6$): δ0.95 (m, 2H), 1.25 (m, 3H), 1.70 (m, 6H), 3.45 (d, 2H, CH$_2$), 4.45 (br, HDO+NH), 6.65 (s, 1H, H4).

6-Chloro-3-(cyclohexylmethyl)amino-4H-thieno[3,2-e]-1,2,4-thiadiazine 1,1-dioxide The title compound was prepared from N-(3-amino-5-chloro-2-thienylsulfonyl)-N'-cyclohexylmethylthiourea by a procedure analogous to the procedure described in example 3-b (yield 68%); mp.>200° C. decomp., $^1$H-NMR (DMSO-d$_6$): δ0.90 (m, 2H), 1.15 (m, 3H), 1.70 (m, 6H), 3.05 (t, 2H, CH$_2$), 7.05 (s, 1H, H-5), 7.25 (br, 1H, NH), 10.95 (br s, 1H, NH). MS: M/e 333 (M+).

Example 10

Ethyl 3-(6-chloro-1,4-dihydro-1,1-dioxothieno[3,2-e]-1λ$^6$,2,4-thiadiazin-3-ylamino)butanoate a) Ethyl 3-{3[(3-amino-5-chlorothien-2-yl)sulfonyl]thioureido}butanoate The title compound was prepared from 3-amino-5-chlorothiophene-2-sulfonamide hydrochloride and ethyl 3-isothiocyanatobutyrate by a procedure analogous to the procedure described in example 3-a (yield 93%); $^1$H-NMR (DMSO-d$_6$): δ1.18 (d, 3H, CH$_3$), 1.20 (t, 3H, CH$_3$), 2.61 (m, 2H, CH$_2$), 4.08 (q, 2H, CH$_2$), 4.58 (m, 1H, CH), 6.46 (br s, 2H, NH$_2$), 6.65 (s, 1H, H-4), 8.34 (br d, 1H, NH), 11.35 (br s, 1H).

b) Ethyl 3-(6-chloro-1,4-dihydro-1,1-dioxothieno[3.2-e]-1λ$^6$,2,4-thiadiazin-3-ylamino)butanoate The title compound was prepared from ethyl 3{3[(3-amino-5-chlorothien-2-yl)sulfonyl]thioureido}butanoate by a procedure analogous to the procedure described in example 3-b except that the product was purified by column chromatography (yield 71%); mp 151–155° C. (ethyl acetate); $^1$H-NMR (DMSO-d$_6$): δ1.18 (t, 3H, CH$_3$), 1.20 (d, 3H, CH$_3$), 2.57 (m, 2H, CH$_2$), 4.07 (q, 2H, CH$_2$), 4.17 (m, 1H, CH), 7.05 (s, 1H, H-5), 7.25 (br, 1H, NH), 10.99 (s, 1H, NH); MS: m/e 351/353 (M+); (C$_{11}$H$_{14}$N$_3$Cl$_1$O$_4$S$_2$.0.2 ethyl acetate) calc. C, 38.36; H, 4.26; N, 11.37; found C, 38.35; H, 4.18; N, 11.58.

Example 11

3-(6-Chloro-1,4-dihydro-1,1-dioxothieno[3,2-e]-1λ$^6$, 2,4-thiadiazin-3-ylamino)butanoic acid Ethyl 3-(6-chloro-1,4-dihydro-1,1-dioxothieno[3,2-e]-1λ$^6$,2,4-thiadiazin-3-ylamino)butanoate (0.5 g. 1.42 mmol) was hydrolyzed to the acid by stirring in 5 ml of 2 N sodium hydroxide for 2 h at room temperature. The solution was treated with decolorising charcoal, filtered and acidified with 4 M hydrochloric acid to pH 2. The resulting precipitate was isolated by filtration, washed with water and dried to give 294 mg (64%) of the title compound; m.p.218–223° C.; $^1$H-NMR (DMSO-d$_6$): δ1.19 (d, 3H, CH$_3$), 2.49 (m, 2H, CH$_2$), 4.10 (m, 1H, CH), 7.06 (s, 1H, H-5), 7.25 (br, 1H, NH), 10.99 (s, 1H, NH), 12.38 (br s, 1H, OH); MS: m/e 305/307 (M–H$_2$O)$^+$; (C$_9$H$_{10}$N$_3$Cl$_1$O$_4$S$_2$) calc. C, 33.39; H, 3.11; N, 12.98; found C, 33.62; H, 3.11; N, 12.81.

Example 12

6-Chloro-3-(3-hydroxy-1-methylpropyl)amino-4H-thieno[3,2-e]-1,2,4-thiadiazine 1,1-dioxide Toluene (5 ml) was cooled to 10° C. and lithium aluminum hydride (114 mg, 3 mmol) was added followed by 0.53 ml of tetrahydrofuran. Ethyl 3-(6-chloro-1,4-dihydro-1,1-dioxothieno[3,2-e]-1λ$_6$,2,4-thiadiazin-3-ylamino)butanoate (352 mg, 1 mmol) was added to the cooled solution and the mixture was stirred for 2 h at 0° C. and then at room temperature over night. The mixture was cooled on an ice bath and 10 ml of water was added dropwise followed by 5–10 ml of 20% sulfuric acid. The mixture was extracted with ether (3×30 ml) and the organic phase was washed with water, dried and evaporated to dryness. The crude product was mixed with the solid that was formed in the aqueous phase and finally purified by column chromatography on silica with ethyl acetate/methanol (9:1) affording 120 mg (39%) of the title compound; m.p.199–203° C.; $^1$H-NMR (DMSO-d$_6$): δ1.14 (d, 3H, CH$_3$), 1.65 (m, 2H, CH$_2$), 3.48 (m, 2H, CH$_2$), 3.90 (m, 1H, CH), 4.60 (br s, 1H, OH), 7.06 (s, 1H, H-5), 7.17 (br, 1H, NH), 10.86 (s, 1H, NH); MS: m/e 309/311 (M$^+$); (C$_9$H$_{12}$N$_3$Cl$_1$O$_3$S$_2$.0.15 ethyl acetate) calc. C, 35.70; H, 4.12; N, 13.01; found C, 35.7; H, 4.1; N. 13.1.

Example 13

(R)-6-Chloro-3-(1-phenylethyl)amino-4H-thieno[3,2-e]-1,2,4-thiadiazine 1,1-dioxide a) (R)-N-(3-Amino-5-chloro-2-thienylsulfonyl)-N'-(1-phenylethyl)thiourea The title compound was prepared from 3-amino-5-chlorothiophene-2-sulfonamide hydrochloride and D-α- methylbenzyl isothiocyanate by a procedure analogous to the procedure described in example 3-a (yield 96% impure product); $^1$H-NMR (DMSO-d$_6$): δ1.46 (d, 3H, CH$_3$), 5.36 (quint, 1H, CH), 6.45 (br s, 2H, NH$_2$), 6.64 (s, 1H, H-4), 7.2–7.4 (m, 5H, ArH), 8.53 (br d, 1H, NH), 11.3 (br s, 1H).

b) (R)-6-Chloro-3-(1-phenylethyl)amino-4H-thieno [3,2-e]-1,2,4-thiadiazine 1,1-dioxide The title compound was prepared from crude (R)-N-(3-Amino-5-chloro-2-thienylsulfonyl)-N'-1-phenylethyl) thiourea by a procedure analogous to the procedure described in example 3-b except that the product was purified by column chromatography on silica with dichloromethane/methanol (19:1), (yield 17%); mp 218–220° C. (ethyl acetate); $^1$H-NMR (DMSO-d$_6$): δ1.48 (d, 3H, CH$_3$), 4.97 (quint, 1H, CH), 7.10 (s, 1H, H-5), 7.2–7.4 (m, 5H, ArH), 7.73 (br, 1H, NH), 10.81 (s, 1H, NH); MS: m/e 341/343 (M+); (C$_{13}$H$_{12}$N$_3$Cl$_1$O$_2$S$_2$) calc. C, 45.68; H, 3.54; N, 12.29; found C, 45.83; H, 3.55; N, 12.04.

Example 14

(S)-3-sec-Butylamino-6-chloro-4H-thieno[3,2-e]-1, 2,4-thiadiazine 1,1-dioxide

A solution of 3,6-dichloro-4H-thieno[3,2-e]-1,2,4-thiadiazine 1,1-dioxide (257 mg, 1.0 mmol) and (S)-(+)-sec-butylamine (0.31 ml, 3.0 mmol) was stirred in 10 ml of abs ethanol for 4 days at 80° C. in a sealed flask. The cooled solution was concentrated in vacuo and the residue was stirred with water (10 ml) followed by adjustment to pH 2 with 4M hydrochloric acid. The initially formed gummy product was crystallized by stirring at 0° C. The precipitate was isolated by filtration, washed with water, and recrystallised from ethyl acetate/methanol followed by drying in vacuo at 30° C. over night to give 181 mg (62%) of the pure title compound; mp 228–230° C. (ethyl acetate); $^1$H-NMR (DMSO-d$_6$): δ0.88 (t, 3H, CH$_3$), 1.14 (d, 3H, CH$_3$), 1,49 (m, 2H, CH$_2$), 3.68 (m, 1H, CH), 7.08 (s, 1H, H-5), 7.13 (br, 1H, NH), 10.73 (br s, 1H, NH); MS: m/e 293/295 (M+); (C$_9$H$_{12}$N$_3$Cl$_1$O$_2$S$_2$) calc. C, 36.79; H, 4.12; N, 14.30; found C, 36.9; H, 4.1; N, 14.2.

Example 15

6-Chloro-3-isopropylamino-4H-thieno[2,3-e]-1,2,4-thiadiazine 1,1-dioxide a) N-[5-Chloro-3-(isopropylthiocarbamoyl) sulfamoylthiophen-2-yl]acetamide Potassium tert-butoxide (135 mg, 1.2 mmol) was added to a solution of N-(5-chloro-3-sulfamoylthiophen-2-yl)-acetamide(255 mg, 1.0 mmol) in dry N,N-dimethylformamide (5 ml) with stirring on an ice bath. After 5 min, isopropyl isothiocyanate (0.128 ml, 1.2 mmol) was added dropwise and the solution was stirred for 30 min at 0° C. and then at room temperature for 3 h. A further amount of potassium tert-butoxide (135 mg, 1.2 mmol) was added to the solution and stirring was continued at room temperature for 1 h. The solvent was evaporated at <50° C., and the residue was taken up in 10 ml of water and the aqueous solution was adjusted to pH 2 with 4 M hydrochloric acid. The resulting precipitate was isolated by filtration, washed with water and dried to give 274 mg (77%) of crude title compound; $^1$H-NMR (DMSO-d$_6$): δ1.12 (d, 6H, 2×CH$_3$), 2.28 (s, 3H, COCH$_3$), 4.21 (m, 1H, NCH), 7.15 (s, 1H, H-4), 8.34 (br d, 1H, NH), 10.26 (s, 1H, NH).

b) 6-Chloro-3-isopropylamino-4H-thieno[2,3-e]-1,2, 4-thiadiazine 1,1-dioxide

Phosgene (0.416 ml, 20% in toluene) was added dropwise to a solution of N-[5-chloro-3-(isopropylthiocarbamoyl) sulfamoylthiophen-2-yl]acetamide(261 mg, 0.73 mmol) and dry triethylamine (0.209 ml, 1.5 mmol) in dry tetrahydrofuran (5 ml) with stirring at 0° C. The mixture was stirred for 1 h at 0° C., and evaporated to dryness. The residue was triturated with 10 ml of water, and the precipitate was isolated by filtration, washed with water and finally deacetylated by stirring in 2 ml of 2 N sodium hydroxide for 90 min at room temperature. The solution was acidified to pH 2 with 4 M hydrochloric acid and the precipitate was filtered off and recrystallised from ethyl acetate with decolorising charcoal affording 44 mg (21%) of the pure title compound; mp 272–274° C. (ethyl acetate); $^1$H-NMR (DMSO-d$_6$): δ1.16 (d, 6H, 2×CH$_3$), 3.85 (m, 1H NCH), 7.23 (s, 1H, H-7), 7.48 (br d, 1H, NH), 11.12 (s, 1H, NH); MS: m/e 279/281 (M+).

Example 16

6-Chloro-3-cyclopentylamino-4H-thieno[2,3-e]-1,2, 4-thiadiazine 1,1-dioxide a) N-[5-Chloro-3-(cyclopentylthiocarbamoyl) sulfamoylthiophen-2-yl]acetamide The title compound was prepared from N-(5-chloro-3-sulfamoylthiophen-2-yl)-acetamide and cyclopentyl isothiocyanate by a procedure analogous to the procedure described in example 15a (yield of crude product: 93%); $^1$H-NMR (DMSO-d$_6$): δ1.3–2.0 (m, 8H, (CH$_2$)$_4$), 2.28 (s, 3H, CH$_3$), 4.32 (sext, 1H, CH), 7.16 (s, 1H, H-4), 8.48 (br d, 1H, NH), 10.23 (br s, 1H, NH).

b) 6-Chloro-3-cyclopentylamino-4H-thieno[2,3-e]-1, 2,4-thiadiazine 1,1-dioxide

The title compound was prepared from N-[5-chloro-3-cyclopentylthiocarbamoyl)sulfamoylthiophen-2-yl] acetamide by a procedure analogous to the procedure described in example 15b (yield 32%); mp 280–282° C. (aqueous ethanol); $^1$H-NMR (DMSO-d$_6$): δ1.4–2.0 (m, 8H, (CH$_2$)$_4$), 3.96 (sext, 1H, CH), 7.23 (s, 1H, H-7), 7.62 (br, 1H, NH), 11.09 (s, 1H, NH); MS: m/e 305/307 (M+).

Example 17

6-Bromo-3-isopropylamino-4H-thieno[3,2-e]-1,2,4-thiadiazine 1,1-dioxide

Bromine (0.12 ml, 2.3 mmol) was added dropwise to a solution of 6-chloro-3-isopropylamino-4H-thieno[3,2-e]-1, 2,4-thiadiazine 1,1-dioxide (280 mg, 1.0 mmol) in 10 ml of acetic acid and the mixture was stirred for 24 h at 100° C. in a sealed flask. The cooled mixture was evaporated to dryness and the residue was triturated with water to give a solid, which was recrystallised from ethanol/water (1:1) affording 118 mg (39%) of the title compound contaminated with 10% of the starting material; mp ca. 279° C. (aqueous ethanol); $^1$H-NMR (DMSO-d$_6$): δ1.16 (d, 6H, 2×CH$_3$), 3.86 (m, 1H, CH), 7.14 (s, 1H, H-5), 7.18 (br, 1H, NH), 10.74 (s, 1H, NH); MS: m/e 323/325 (M+).

Example 18

3-Isopropylamino-4H-thieno[3,2-e]-1,2,4-thiadiazine 1.1-dioxide

Powdered potassium hydroxide (128 mg, 2.28 mmol) was added to a solution of 6-chloro-3-isopropylamino-4H-thieno

[3,2-e]-1,2,4-thiadiazine 1,1-dioxide (319 mg, 1.14 mmol) in 25 ml of methanol and the mixture was hydrogenated at room temperature and atmospheric pressure for 3 days with 150 mg of 10% palladium on carbon. The catalyst was removed by filtration and washed with ethanol and water. The combined filtrate was acidified with 4 M hydrochloric acid and evaporated to dryness. The residue was recrystallised from water/ethanol and finally from ethyl acetate with decolorising charcoal affording the title compound contaminated with starting material, which could be removed by silica gel column chromatography; $^1$H-NMR (DMSO-d$_6$): δ1.16 (d, 6H, 2×CH$_3$), 3.88 (m, 1H, CH), 6.95 (d, 1H, H-5), 7.03 (br d, 1H, NH), 7.88 (d, 1H, H-6), 10.70 (br s, 1H).

Example 19

3-Isopropylamino-7-methyl-4H-thieno[2,3-e]-1,2,4-thiadiazine 1,1-dioxide a) Cyanomethanesulfonamide Dry THF (200 ml) was saturated with ammonia at −10° C. Then a solution of cyanomethane-sulfonyl chloride (13.9 g; prepared according to Sammes et al, J.Chem.Soc., 1971, 2151–5155) in 10 ml of dry THF was added in small portions with stirring over 20 min at −10° C. After the addition the temperature was rised to 0° C. and the reaction mixture was filtered. Removal of the solvent from the filtrate and purification of the residue by column chromatography on silica gel eluted with ethyl acetate gave the title compound as beige crystals; m.p. 97–99° C.; IR (KBr), ν (cm$^{-1}$): 3316, 3328 (N—H), 2266 (C≡N), 1371, 1151 (SO$_2$).

b) 2-Amino-4-methyl-thiophene-3-sulfonamide

A mixture of cyanomethanesulfonamide (1.0 g), 2,5-dihydroxy-2,5-dimethyl-1,4-dithiane (0.75 g), and triethylamine (100 μl) in absolute ethanol (7 ml) was heated at 45–50° C. under nitrogen for 3 h. Then the solvent was evaporated and the residue partitioned in water (30 ml) and ethyl acetate (50 ml). The aqueous phase was extracted with 4×50 ml of ethyl acetate. The combined ethyl acetate phases were dried over sodium sulfate and evaporated. The residue was purified by column chromatography on silica gel eluted with ethyl acetate. The title compound was obtained as a yellow solid, yield 0.65 (41%); m.p. 142–144° C.; $^1$H-NMR (CD$_3$OD), δ(ppm): 7.19 (s, 1 H, C(5)H), 4,88 (br, 4 H, SO$_2$NH$_2$+H$_2$O), 4.71 (s, 2 H, NH$_2$), 2.41 (s, 3 H, CH$_3$); MS: 192 (M$^+$), 112 (M$^+$—SO$_2$NH$_2$), 72 (CH$_3$—C$_2$HS$^+$).

c) N-(2-Amino-4-methyl-3-thienylsulfonyl)-N'-isopropylthiourea

A mixture of 2-amino-4-methyl-thiophene-3-sulfonamide (0.30 g), potassium carbonate (0.32 g), and isopropyl isothiocyanate (272 μl) in dry acetone (5 ml) under nitrogen was heated at 50–55° C. overnight. Then the solvent was evaporated and the residue was dissolved in water (15 ml); pH was adjusted to 2 by addition of 4 M hydrochloric acid, and the mixture was stirred for 30 min. The precipitated crystals were filtered off, rinsed with a small amount of water and dried to give 0.24 g (yield 54%) of the title compound; m.p. 118–120° C.

d) 3-Isopropylamino-7-methyl-4H-thieno[2,3-e]-1,2,4-thiadiazine 1,1-dioxide

A 20% solution of phosgene in toluene (715 μl) was added to a stirred and cooled solution of N-(2-amino-4-methyl-3-thienylsulfonyl)-N'-isopropylthiourea (0.22 g) and triethylamine (313 μl) in dry THF (5 ml) the temperature being kept below 5° C. After stirring for 1.5 h the mixture was evaporated and triturated with 10 ml of water. The precipitate was collected by filtration and dried to give 0.14 g of crude product. The crystals were heated at 70° C. with 5 ml of ethyl acetate and the resulting mixture was cooled to 0° C. for 10 min and then filtered. The filter cake was rinsed with a minute amount of ethyl acetate and dried to give 0.087 g (yield 45%) of the title compound as tan crystals; m.p. 152–154° C.; $^1$H-NMR (DMSO-d$_6$): δ(ppm): 7.10 (br d, 1 H, NH), 6.61 (s, 1 H, N(4)H), 6.52 (s, 1 H, C(6)H), 3.89 (m, 1 H, CH), 2.32 (s, 3 H, CH$_3$), 1.18 (d, 6 H, CH$_3$).

Example 20

6-Chloro-3-cyclobutylamino-4H-thieno[3,2-e]-1,2,4-thiadiazine 1,1-dioxide

A solution of 3,6-dichloro-4H-thieno[3,2-e]-1,2,4-thiadiazine 1,1-dioxide (257 mg, 1.0 mmol) in cyclobutylamine (1.0 ml) was stirred for 18 h at 90° C. in a sealed flask. The cooled solution was concentrated in vacuo and the residue was stirred with water (10 ml) at 0° C. followed by adjustment to pH 2 with 4M hydrochloric acid. The product was isolated by filtration, washed with water, and recrystallised from methanol/ethyl acetate followed by drying in vacuo at room temperature to give 155 mg (53%) of the pure title compound; mp 315–317° C. dec.; $^1$H-NMR (DMSO-d$_6$): δ1.58–1.75 (m, 2H), 1.89–2.05 (m, 2H), 2.19–2.30 (m, 2H), 4.16 (m, 1H), 7.06 (s, 1H), 7.62 (br s, 1H), 10.83 (br s, 1H); MS: m/e 291/293 (M$^+$); (C$_9$H$_{10}$N$_3$Cl$_1$O$_2$S$_2$) calc C, 37.05; H, 3.45; N, 14.40; found C, 37.18; H, 3.48; N, 14.19.

Example 21

6-Chloro-3-(2-hydroxyethyl)amino-4H-thieno[3,2-e]-1,2,4-thiadiazine 1,1-dioxide

A solution of 3,6-dichloro-4H-thieno[3,2-e]-1,2,4-thiadiazine 1,1-dioxide (206 mg, 0.8 mmol) in ethanolamine (1.0 ml) was stirred for 18 h at 100° C. in a sealed flask. The cooled solution was concentrated in vacuo and the residue was stirred with water (5 ml) at 0° C. followed by adjustment to pH 2 with 4M hydrochloric acid. The product was isolated by filtration, washed with water, and recrystallised from ethanol/water to give 135 mg (60%) of the pure title compound; mp 260–261° C. dec.; $^1$H-NMR (DMSO-d$_6$): δ3.26 (distorted q, 2H), 3.50 (t, 2H), 4.85 (br s, 1H), 7.07 (s, 1H), 7.20 (br s, 1H), 10.9 (br s, 1H); MS: m/e 281/283 (M$^+$); (C$_7$H$_8$N$_3$Cl$_1$O$_3$S$_2$) calc C, 29.84; H, 2.86; N, 14.91; found C, 30.13; H, 2.84; N, 14.79.

Example 22

(±)-3-exo-Bicyclo[2,2,1]hept-2-ylamino-6-chloro-4H-thieno[3,2-e]-1,2,4-thiadiazine 1,1dioxide A solution of 3,6-dichloro-4H-thieno[3,2-e]-1,2,4-thiadiazine 1,1-dioxide (206 mg, 0.8 mmol) in exo-2-aminonorbornane (1.0 ml) was stirred for 20 h at 100° C. in a sealed flask. The mixture was stirred with water (10 ml) at 0° C. followed by adjustment to pH 2 with 4M hydrochloric acid. The product was isolated by filtration, washed with water, and recrystallised from ethyl acetate/methanol to give 168 mg (63%) of the pure title compound; mp 323–324° C. dec.; $^1$H-NMR (DMSO-d$_6$): δ1.05–1.55 (m, 7H), 1.68–1.77 (m, 1H), 2.18–2.28 (m, 2H), 3.51 (m, 1H), 7.09 (s, 1H), 7.2 (br s, 1H), ca.10.5 (br s, 1H); MS: m/e 331/333(M$^+$); (C$_{12}$H$_{14}$N$_3$Cl$_1$O$_2$S$_2$) calc C, 43.43; H, 4.25; N, 12.66; found C 43.67; H, 4.26; N, 12.55.

Example 23

(R)-6-Chloro-3-(2-hydroxypropyl)amino-4H-thieno[3,2-e]-1,2,4-thiadiazine 1,1-dioxide A solution of 3,6-dichloro-4H-thieno[3,2-e]-1,2,4-thiadiazine 1,1-dioxide (200 mg, 0.78 mmol) in (R)-(−)-1-amino-2-propanol (1.0 ml) was stirred for 18 h at 100° C. in a sealed flask. The cooled solution was stirred with water (3 ml) at 0° C. followed by adjustment to pH 2 with 4M hydrochloric acid. The product was isolated by filtration, washed with water, and dried in vacuo at room temperature to give 170 mg (74%) of the pure title compound; mp 210–211° C.; $^1$H-NMR (DMSO-d$_6$): δ1.08 (d, 3H), 3.0–3.1 (m, 1H), 3.15–3.25 (m, 1H), 3.72–3.82 (m, 1H), 4.91 (br s, 1H), 7.09 (s, 1H), 7.14 (br s, 1H), 10.95 (br s, 1H); MS: m/e 297/295(M$^+$); (C$_8$H$_{10}$N$_3$Cl$_1$O$_3$S$_2$.0.5 H$_2$O) calc C, 31.53; H, 3.64; N, 13.79; found C, 31.57; H, 3.58; N, 13.58.

Example 24

6-Bromo-3-isopropylamino-4H-thieno[3,2-e]-1,2,4-thiadiazine 1,1-dioxide

Bromine (1.26 ml, 25 mmol) was added dropwise to a solution of 6-chloro-3-isopropylamino-4H-thieno[3,2-e]-1,2,4-thiadiazine 1,1-dioxide (2.3 g, 8.2 mmol) in 25 ml of acetic acid and the mixture was stirred for 48 h at 100° C. in a sealed flask. The cooled mixture was evaporated to dryness and the residue which consisted of two major products was triturated with water to give a solid, which was recrystallised from ethyl acetate/methanol with decolorising charcoal to afford 538 mg (20%) of the title compound. An analytically pure sample was obtained by preparative hplc on a Source RPC 15 column using acetonitrile/water (20:80) with 0.1% TFA as eluent; mp 282–283° C.; $^1$H-NMR (DMSO-d$_6$): δ1.16 (d, 6H), 3.86 (m, 1H), 7.14 (s, 1H), 7.18 (br, 1H), 10.74 (s, 1H); MS: m/e 323/325 (M$^+$); (C$_8$H$_{10}$N$_3$Br$_1$O$_2$S$_2$); calc C, 29.64; H, 3.11; N, 12.96; found C, 29.49; H, 3.04; N, 12.59.

Example 25

5,6-Dibromo-3-isopropylamino-4H-thieno[3,2-e]-1,2,4-thiadiazine 1,1-dioxide

The mother liquor from the crystallisation of 6-bromo-3-isopropylamino-4H-thieno[3,2-e]-1,2,4-thiadiazine 1,1-dioxide described above was evaporated to dryness and the residue was purified by chromatography on silica with dichloromethane/methanol (95:5). Recrystallisation from ethyl acetate gave 270 mg (8%) of pure title compound; mp 250–251°C.; $^1$H-NMR (DMSO-d$_6$): δ1.18 (d, 6H), 3.86 (m, 1H), 7.18 (br, 1H), 10.31 (s, 1H); MS: m/e 405/403/401 (M$^+$); (C$_8$H$_9$N$_3$Br$_2$O$_2$S$_2$); calc C, 23.84; H, 2.25; N, 10.42; found C, 24.14; H, 2.18; N, 10.25.

Example 26

6-Chloro-3-cyclohexylamino-4H-thieno[3,2-e]-1,2,4-thiadiazine 1,1-dioxide a) N-(3-Amino-5-chloro-2-thienylsulfonyl)-N'-(cyclohexyl)thiourea The title compound was prepared from 3-amino-5-chlorothiophene-2-sulfonamide hydrochloride and cyclohexyl isothiocyanate by a procedure analogous to the procedure described in example 3-a (yield 78%); $^1$H-NMR (DMSO-d$_6$): δ1.1–1.9 (m, 10H), 4.0 (m, 1H), 6.45 (br s, 2H), 6.66 (s, 1H), 8.05 (br d, 1H), 11.2 (br s, 1H).

b) 6-Chloro-3-cyclohexylamino-4H-thieno[3,2-e]-1,2,4-thiadiazine 1,1-dioxide

The title compound was prepared from N-(3-Amino-5-chloro-2-thienylsulfonyl)-N'-(cyclohexyl)thiourea by a procedure analogous to the procedure described in example 3-b (yield 66%); mp 282–284° C. (ethyl acetate/methanol); $^1$H-NMR (DMSO-d$_6$): δ1.1–1.9 (m, 10H), 3.55 (m, 1H), 7.08 (s, 1H), 7.19 (br, 1H), 10.73 (br s, 1H); MS: m/e 321/319 (M$^+$); (C$_{11}$H$_{14}$N$_3$Cl$_1$O$_2$S$_2$) calc. C, 41.31; H, 4.41; N, 13.14; found C, 41.66; H, 4.45; N, 12.99.

Example 27

6-Chloro-3-(furan-2-ylmethyl)amino-4H-thieno[3,2-e]-1,2,4-thiadiazine 1,1-dioxide a) N-(3-Amino-5-chloro-2-thienylsulfonyl)-N'-(furan-2-ylmethyl)thiourea The title compound was prepared from 3-amino-5-chlorothiophene-2-sulfonamide hydrochloride and furfuryl isothiocyanate by a procedure analogous to the procedure described in example 3-a (yield of crude product: 92%).

b) 6-Chloro-3-(furan-2-ylmethyl)amino-4H-thieno[3,2-e]-1,2,4-thiadiazine 1,1-dioxide The title compound was prepared from crude N-(3-Amino-5-chloro-2-thienylsulfonyl)-N'-(furan-2-ylmethyl)thiourea by a procedure analogous to the procedure described in example 3-b except that the product was purified by column chromatography on silica with dichloromethane/methanol (19:1), (yield 11%); mp 224–225° C.; $^1$H-NMR (DMSO-d$_6$): δ4.41 (d, 2H), 6.33 (m, 1H), 6.41 (m, 1H), 7.05 (s, 1H), 7.62 (br s, 1H), 7.75 (br t, 1H), 11.2 (br s, 1H); (C$_{10}$H$_8$N$_3$Cl$_1$O$_3$S$_2$); calc C, 37.80; H, 2.54; N, 13.22; found C, 37.87; H, 2.51; N, 13.10).

Example 28

6-Cyano-3-isopropylamino-4H-thieno[3,2-e]-1,2,4-thiadiazine 1,1-dioxide

To a solution of 6-bromo-3-isopropylamino-4H-thieno[3,2-e]-1,2,4-thiadiazine 1,1-dioxide (243 mg, 0.75 mmol) in dry N,N-dimethylformamide (2 ml) was added copper(I) cyanide (135 mg, 1.5 mmol) and the mixture was heated at 150° C. for 2 h under nitrogen. The dark mixture was allowed to cool to room temperature and water was added. The suspension was made basic by the addition of 1 N sodium hydroxide, filtered and the filtrate was acidified by the addition of 4 M hydrochloric acid. The resulting precipitate was purified by preparative hplc on a Source RPC 15 column using acetonitrile/water (20:80) with 0.1% TFA as eluent to afford 4 mg (2%) of the pure title compound; LC-MS: m/e 271 ((M+1)$^+$).

Example 29

6-Bromo-3-cyclopentylamino-4H-thieno[3,2-e]-1,2,4-thiadiazine 1,1-dioxide

Bromine (0.12 ml, 2.3 mmol) was added dropwise to a solution of 6-chloro-3-cyclopentylamino-4H-thieno[3,2-e]-1,2,4-thiadiazine (305 mg, 1.0 mmol) in acetic acid (10 ml) and the mixture was stirred for 21 h at 100° C. in a sealed flask. The cooled mixture was evaporated to dryness and the residue was triturated with water to give a solid, which was recrystallised from ethyl acetate and ethanol affording the title compound (166 mg, 47%) contaminated with 33% of the starting material. Purification by preparative HPLC gave the title compound (65 mg, 18%) contaminated with 3% of the starting material. $^1$H-NMR (DMSO): δ10.7 (s, 1H, NH); 7.35 (br s, 1H, NH); 7.13 (s, 1H, H-7); 4.00 (sextet, 1H); 1.9 (m, 2H); 1.7 to 1.4 ppm (m, 6H). Decomp.: 287–294° C.

Example 30

6-Chloro-3-(2-methylallyl)amino-4H-thieno[3,2-e]-1,2,4-thiadiazine 1,1-dioxide

A solution of 3,6-dichloro-4H-thieno[3,2-e]-1,2,4-thiadiazine 1,1-dioxide (128 mg, 0.5 mmol) in methallylamine (0.5 ml) was stirred for 48 h at 90° C. in a sealed flask. The cooled solution was concentrated in vacuo and the residue was stirred with water (3 ml) followed by adjustment to pH 2 with 4M hydrochloric acid. The product was isolated by filtration and washed with water, to give 92 mg (64%) of the pure title compound; mp 224–226° C. (dec.); $^1$H-NMR (DMSO-d$_6$): δ1.72 (s, 3H), 3.75 (d, 2H), 4.83 (s, 2H), 7.05 (s, 1H), 7.45 (br s, 1H), 11.0 (br s, 1H).

What is claimed is:
1. A compound selected from the following:
7-Cyano-6-methyl-3-propylamino-4H-thieno[2,3-e]-1,2,4-thiadiazine 1,1-dioxide
6-Chloro-3-isopentylamino-4H-thieno[3,2-e]-1,2,4-thiadiazine 1,1-dioxide
6-Chloro-3-(1-methylheptyl)amino-4H-thieno[3,2-e]-1,2,4-thiadiazine 1,1-dioxide
6-Chloro-3-(1-ethylpentyl)amino-4H-thieno[3,2-e]-1,2,4-thiadiazine 1,1-dioxide
6-Chloro-3-(2-methylbutyl)amino-4H-thieno[3,2-e]-1,2,4-thiadiazine 1,1-dioxide
6-Chloro-3-(1-methylhexyl)amino-4H-thieno[3,2-e]-1,2,4-thiadiazine 1,1-dioxide
6-Chloro-3-cyclopentylamino-4H-thieno[3,2-e]-1,2,4-thiadiazine 1,1-dioxide
6-Chloro-3-cyclohexylmethylamino-4H-thieno[3,2-e]-1,2,4-thiadiazine 1,1-dioxide
Ethyl 3-(6-chloro-1,4-dihydro-1,1-dioxothieno[3,2-e]-1$\lambda^6$,2,4-thiadiazin-3-ylamino)butanoate
3-(6-Chloro-1,4-dihydro-1,1-dioxothieno[3,2-e]-1$\lambda^6$,2,4-thiadiazin-3-ylamino)butanoic acid
6-Chloro-3-(3-hydroxy-1-methylpropyl)amino-4H-thieno[3,2-e]-1,2,4-thiadiazine 1,1-dioxide
(R)-6-Chloro-3-(1-phenylethyl)amino-4H-thieno[3,2-e]-1,2,4-thiadiazine 1,1-dioxide
(S)-3-sec-Butylamino-6-chloro-4H-thieno[3,2-e]-1,2,4-thiadiazine 1,1-dioxide
6-Chloro-3-isopropylamino-4H-thieno[2,3-e]-1,2,4-thiadiazine 1,1-dioxide
6-Chloro-3-cyclopentylamino-4H-thieno[2,3-e]-1,2,4-thiadiazine 1,1-dioxide
6-Bromo-3-isopropylamino-4H-thieno[3,2-e]-1,2,4-thiadiazine 1,1-dioxide
3-Isopropylamino-4H-thieno[3,2-e]-1,2,4-thiadiazine 1,1-dioxide
6-Fluoro-3-isopropylamino-4H-thieno[3,2-e]-1,2,4-thiadiazine 1,1-dioxide
3-Cyclobutylamino-5,6-dimethyl-4H-thieno[3,2-e]-1,2,4-thiadiazine 1,1-dioxide
3-Cyclopentylamino-5,6-dimethyl-4H-thieno[3,2-e]-1,2,4-thiadiazine 1,1-dioxide
3-Isopropylamino-6,7-dimethyl-4H-thieno[2,3-e]-1,2,4-thiadiazine 1,1-dioxide
3-Cyclobutylamino-6,7-dimethyl-4H-thieno[2,3-e]-1,2,4-thiadiazine 1,1-dioxide
3-Cyclopentylamino -6,7-dimethyl-4H-thieno[2,3-e]-1,2,4-thiadiazine 1,1-dioxide
5-Chloro-3-isopropylamino-4H-thieno[3,2-e]-1,2,4-thiadiazine 1,1-dioxide
5-Chloro-3-propylamino-4H-thieno[3,2-e]-1,2,4-thiadiazine 1,1-dioxide
5-Chloro-3-cyclopentylamino-4H-thieno[3,2-e]-1,2,4-thiadiazine 1,1-dioxide
5-Chloro-6-methyl-3-isopropylamino-4H-thieno[3,2-e]-1,2,4-thiadiazine 1,1-dioxide
6-chloro-3-isopropylamino-5-methyl-4H-thieno[3,2-e]-1,2,4thiadiazine 1,1-dioxide
6-chloro-3-cyclopentylamino-5-methyl-4H-thieno[3,2-e]-1,2,4-thiadiazine 1,1-dioxide
6-Fluoro-3-propylamino-4H-thieno[3,2-e]-1,2,4-thiadiazine 1,1-dioxide
6-Fluoro-3-cyclopentylamino-4H-thieno[3,2-e]-1,2,4-thiadiazine 1,1-dioxide
5-Fluoro-3-propylamino-4H-thieno[3,2-e]-1,2,4-thiadiazine 1,1-dioxide or
5-Fluoro-3-isopropylamino-4H-thieno[3,2-e]-1,2,4-thiadiazine 1,1-dioxide.
2. A pharmaceutical composition comprising a compound of claim 1 together with one or more pharmaceutically acceptable carriers or diluents.
3. A method of treating hyperinsulinemia or diabetes, comprising administering to a subject in need thereof an effective amount of a compound of claim 1.

* * * * *